(12) United States Patent
Teixeira et al.

(10) Patent No.: US 9,271,808 B2
(45) Date of Patent: Mar. 1, 2016

(54) ORTHODONTIC METHODS AND DEVICES

(75) Inventors: Cristina C. Teixeira, New York, NY (US); Mani Alikhani, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/806,376

(22) Filed: Aug. 11, 2010

(65) Prior Publication Data

US 2011/0065060 A1    Mar. 17, 2011

Related U.S. Application Data

(60) Provisional application No. 61/273,900, filed on Aug. 11, 2009.

(51) Int. Cl.
*A61C 7/00* (2006.01)
*A61C 3/00* (2006.01)
*A61B 17/16* (2006.01)

(52) U.S. Cl.
CPC ... *A61C 7/00* (2013.01); *A61C 3/00* (2013.01); *A61B 17/1604* (2013.01)

(58) Field of Classification Search
CPC ......... A61C 7/00; A61C 3/00; A61B 17/1604
USPC .............................. 433/24, 165–166
See application file for complete search history.

(56) References Cited

U.S. PATENT DOCUMENTS

| | | |
|---|---|---|
| 1,328,459 A | 1/1920 | Smith |
| 4,347,054 A | 8/1982 | Kraus et al. |
| 4,433,956 A | 2/1984 | Witzig |
| 4,482,318 A | 11/1984 | Forster |

(Continued)

FOREIGN PATENT DOCUMENTS

| | | |
|---|---|---|
| CA | 2231116 | 8/1999 |
| KR | 20050081979 A | 8/2005 |
| WO | 0182817 | 11/2001 |

OTHER PUBLICATIONS

King et al., Later Orthodontic Appliance Reactivation Stimulates Immediate Appearance of Osteoclasts and Linear Tooth Movement, American Journal of Orthodontics and Dentofacial Orthopedics, vol. 114, Issue 6, pp. 692-697, 1998.*

(Continued)

*Primary Examiner* — Ralph Lewis

(74) *Attorney, Agent, or Firm* — Klauber & Jackson LLC

(57) ABSTRACT

The present invention provides methods for moving a tooth to a desired position within a patient's mouth using orthodontics including perforating tissue in the oral cavity sufficient to induce an inflammatory response. The perforations may be made in any area of the maxilla or mandible, and any number of perforations may be made that are preferably 0.5 to 1.5 mm diameter, and preferably 1 to 3 mm deep. The invention also provides a device that may be used in conjunction with slow-speed rotary instruments or with manual drivers for providing the perforations. The device has a drill that makes the perforations and a stop that prevents the drill from penetrating the jaw bone beyond a predetermined depth. The invention also provides a kit that supplies the professional with the necessary components in a sealed container to carry out the osteoperforations. The kit may include hand held and rotatory perforating devices, anesthetic, and a soft tissue punch.

22 Claims, 11 Drawing Sheets

(56) References Cited

U.S. PATENT DOCUMENTS

| | | | |
|---|---|---|---|
| 4,483,674 A | 11/1984 | Schutz | |
| 4,747,824 A * | 5/1988 | Spinello | 604/512 |
| 4,828,113 A | 5/1989 | Friedland et al. | |
| 4,944,677 A * | 7/1990 | Alexandre | 433/165 |
| 5,002,485 A | 3/1991 | Aagesen | |
| 5,154,611 A | 10/1992 | Calvin | |
| 5,281,133 A | 1/1994 | Farzin-Nia | |
| 5,439,377 A | 8/1995 | Milanovich | |
| 5,472,344 A | 12/1995 | Binder et al. | |
| 5,547,657 A | 8/1996 | Singleton et al. | |
| 6,109,916 A | 8/2000 | Wilcko et al. | |
| 7,329,122 B1 | 2/2008 | Scott | |
| 2006/0116561 A1 | 6/2006 | Tricca et al. | |
| 2007/0084742 A1 | 4/2007 | Miller et al. | |
| 2007/0298375 A1 | 12/2007 | Hirsch et al. | |
| 2008/0102415 A1 | 5/2008 | Scott | |

OTHER PUBLICATIONS

Iino, et al., Journal of Orthodontics and Dentofacial Orthopedica, vol. 131, Issue 4, pp. 448.e1-; p. 448.e2-e4 (2007).
Adachi et al., Biol Pharm Bull (1994) 17: 1554-1560.
Alhashimi et al., J Interferon Cytokine Res (2000) 20(1): 7-12.
Anholm et al., CDAJ (1986) 14: 7-11.
Arend et al., Immunol Rev (2008) 223: 20-38.
Arias et al., Am J Orthod Dentofacial Orthop (2006) 130(3): 364-70.
Bai et al., Tissue Antigens (2007) 70: 390-397.
Basaran et al., Am J Orthod Dentofacial Orthop (2006) 130: E1-6.
Bishara et al., Am J Orthod Dentofac Orthop (1987) 91(1): 3-14.
Bolander, Proc Soc Exp Biol Med (1992) 200: 165-170.
Bossu et al., J Neurol Neurosurg Psychiatry (2007) 78: 807-811.
Busti et al., Pharmacotherapy (2005) 25: 1566-1591.
Chao et al., Acta Anat (Basel) (1988) 132: 304-309.
Chung et al., J Chin Orthod (2001) 35: 331-339.
Davidovich et al., Dent Clin North Am (1988) 32(3): 411-35.
de Sa AR et al., Oral Surg Oral Med Oral Pathol Oral Radiol Endod (2003) 96: 356-360.
Dienz et al., Clin Immunol (2009) 130: 27-33.
Fischer et al., Angle Orthod (2007) 77: 417-420.
Frost, Henry Ford Hosp Med Bull (1965) 13: 161-172.
Frost, Henry Ford Hosp Med J (1983) 31(1): 3-9.
Frost, Part II Clin Orthop Relat Res (1989a) 248: 294-309.
Frost, Part I Clin Orthop Relat Res (1989b) 248: 283-93.
Gantes et al., J Periodontol (1990) 61: 234-238.
Garlet et al., Eur J oral Sci (2007) 115(5): 355-62.
Germec et al., Angle Orthodontist (2006) 76: 882-890.
Glantschnig et al., Cell Death Differ (2003) 10(10): 1165-77.
Han et al., Glia (2000) 30: 1-10.
Handelman, Angle Orthodontic 678 (4) 291-305.
Hinton et al., Am J Orthod (1986) 89: 492-498.
Hwang et al., Am J Orthod Dentofacial Orthop (2001) 120: 209-16.
Ito et al., J Immunol (1999) 162: 4260-4265.
Jager et al., Eur J Orthod (2005) 27: 1-11.
Jang et al., Clin Exp Rheumatol (2005) 23: S59-63.
Kao et al., J Immunol (2005) 175: 6676-6685.
Kawasaki et al., Orthod Craniofac Res (2006) 9: 137-142.
Khapli et al., J Immunol (2003) 171: 142-151.
King et al., Am J Orthod Dentofacial Orthop (1991) 99: 456-465.
Kitaura et al., J Dent Res (2008) 87: 396-400.
Knupfer et al., Immunol Cell Biol (2008) 86: 87-91.
Kole, Oral Surg oral Med Oral Pathol (1959) 12: 515-529.
Krishnan et al., Am J Orthod Dentofacial Orthop (2006a) 129: 469.31-469e32.
Krishnan et al., J Dent Res (2009) 88(7): 597-608.
Lean et al., J Cell Biochem (2002) 87: 386-393.
Leng et al., Int J Biochem Cell Biol (1997) 29: 1059-1062.
Liou et al., Am J Orthod Dentofacial Orthop (2000) 117: 391-8.
Luster, N. Engl J Med (1998) 338: 436-445.
Meikle, Eur J Orthod (2006) 28: 221-240.
Mermut et al., Angle Orthod (2007) 77: 135-141.
Piemonti et al., Diabetes (2002) 51: 55-65.
Ren et al., Eur J Oral Sci (2008) 116(2): 89-97.
Ren et al., J Periodontol (2007) 78(3): 453-8.
Saito et al., Am J Orthod Dentofacial Orthop (1991) 99(3): 226-40.
Sallusto et al., J Exp Med (1998) 187: 875-883.
Schneider et al., Immunol Rev (2004) 202: 49-66.
Seidenberg et al., Pharmacol Res (2004) 50(2): 151-6.
Shih et al., Bone (1985) 6(5): 377-9.
Shireman, J Vasc Surg (2007) 45 Suppl A: A48-56.
Uematsu et al., J Dent res (1996) 75: 562-567.
Verna et al., Bone (1999) 24(4): 371-9.
Vignery et al., Anat Rec (1980) 196: 191-200.
Wilcko et al., World J. Orthod (2003) 4: 197-205.
Wilcko et al., Int J Perio & Rest Dent (2001) 21: 9-19.
Williams et al., Biomaterials (1984) 5: 347-351.
Xu et al., Ann Acad Med Singapore (2007) 36: 91-95.
Yaffe et al., J Periodontol (1994) 65(1): 79-83.
Yamamoto et al., J Periodontal Res (2006) 41: 554-559.
Yao et al., J Biol Chem (2008) 283(15): 9917-24.
Yen et al., J Oral Maxillofac Surg (2003) 61: 1346-1350.
Yoshimatsu et al., EJ Bone Miner Meteabl (2006) 24(1): 20-7.
Rubin, et al., "Inhibition of osteopenia by low magnitude, high-frequency mechanical stimuli", DDT, 2001; 6(16): 848-858.
Murphy, "In vivo tissue engineering for othodontists: a modest first step", Biological Mechanisms of Tooth Eruption, Resorption and Movement, 2006, pp. 385-410.

* cited by examiner

FIG. 1A
FIG. 1B
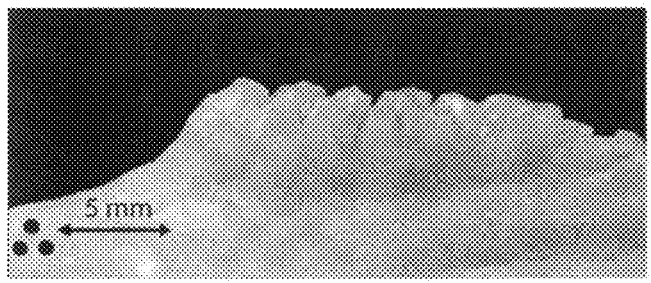
FIG. 1C
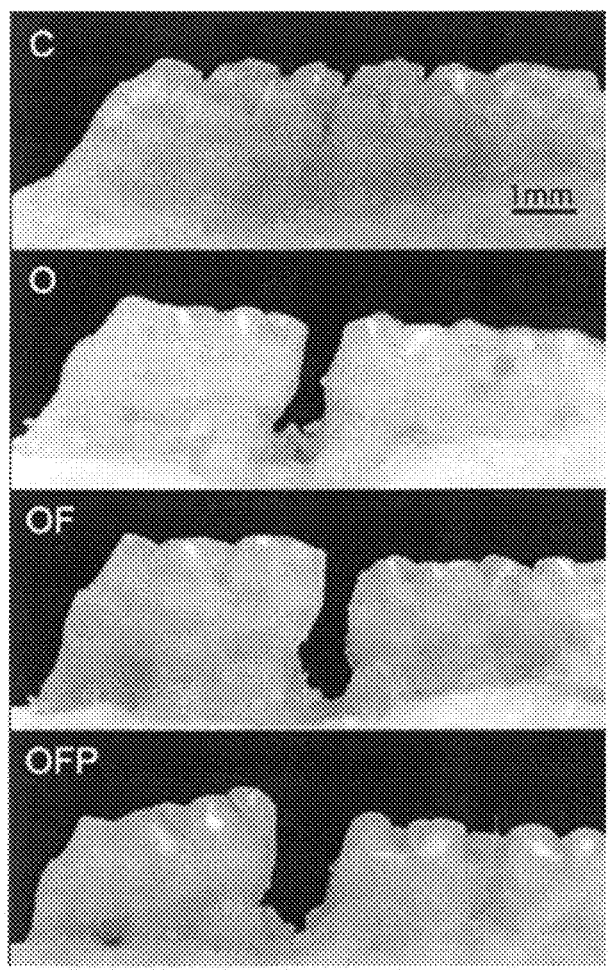

FIG. 5A
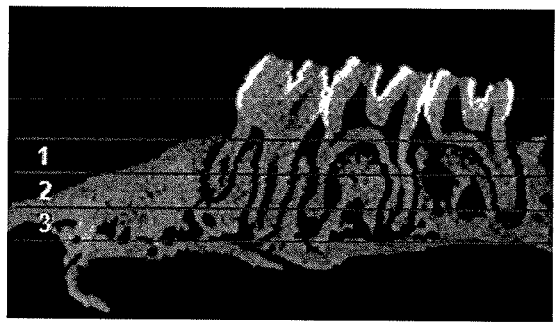
FIG. 5C
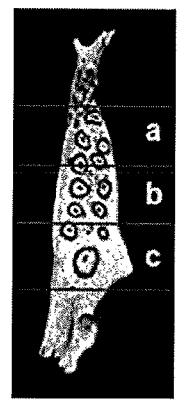
FIG. 5B
| | Zones | a | b | c |
|---|---|---|---|---|
| C | 1 | 77.9 | 69.9 | 45.8 |
| | 2 | 84.3 | 74.1 | 55.8 |
| | 3 | 84.0 | 72.9 | 52.9 |
| | Mean | 82.1 | 72.3 | 51.5 |
| | Zones | a | b | c |
| O | 1 | 71.0 | 53.2 | 50.0 |
| | 2 | 78.8 | 54.9 | 41.6 |
| | 3 | 81.0 | 64.2 | 42.9 |
| | Mean | 76.9\* | 57.4\* | 44.8\* |
| | Zones | a | b | c |
| O F | 1 | 67.5 | 51.4 | 49.3 |
| | 2 | 75.2 | 51.6 | 42.2 |
| | 3 | 78.8 | 62.8 | 41.8 |
| | Mean | 73.9\* | 55.2\* | 44.5\* |
| | Zones | a | b | c |
| O F P | 1 | 30.5 | 22.3 | 38.9 |
| | 2 | 34.6 | 31.8 | 36.4 |
| | 3 | 34.0 | 39.3 | 32.9 |
| | Mean | **33.0\*\*** | **31.1\*\*** | **35.9\*\*** |

Before

Osteoperforation example

Osteoperforation

A  B

ORTHODONTIC METHODS AND DEVICES

CROSS REFERENCE TO RELATED APPLICATIONS

The present application claims the benefit under 35 U.S.C. §119(e) of U.S. provisional application 61/273,900, filed Aug. 11, 2009, the disclosure of which is herein incorporated by reference.

FIELD OF THE INVENTION

The present invention provides methods for performing dental procedures including orthodontic procedures and devices useful for performing such procedures.

BACKGROUND OF THE INVENTION

It was estimated that in 2007, more than 75% of U.S. population was over 18. Today, increasing numbers of adults are seeking orthodontic treatment to enhance the social and psychological status of their life. Treatment of these patients is complicated by the fact that the correction of their malocclusion orthodontically is limited to the dento-alveolar element, since any opportunity for control over their growth and development has passed. While simple cases can be treated by orthodontics treatment alone, the severity of malocclusion in many adults is beyond orthodontics treatment, and can only be addressed through combination with orthognatic surgery. Unfortunately, orthognatic surgery by itself is very expensive, and due to extensive bone cuts in upper and lower jaws can be accompanied by many complications. Therefore at present, there is no other treatment modality for these groups of patients.

It is certainly common for a patient to need an alignment of one or more teeth and, through typically, one method of carrying out such alignment or movement of a tooth is through the use of braces that are installed to the teeth and which include wires and other tension devices, such as rubber bands and coils, to exert a continual tension on the tooth to move the tooth or teeth in to the desired position. One of the problems, however is that the use of braces to move the teeth can take a long period of time, some times 3-4 years, and the patient must continue to wear those braces throughout these long periods. The wearing of braces is sometime difficult for patients, particular adults, who do not like the appearance of the braces and do not like the discomfort. In addition it has been shown that having braces for long time can increase the risk of root resorption and loss of alveolar bone.

One of the reasons for the lengthy period of time is that the tooth needs to move within the jaw bone, which includes the alveolar bone, that contains the tooth sockets, and the cortical plate encasing the dento-alveolar component. In effect, the tooth cannot move until the alveolar bone has been remodeled and that simply takes considerable time. It would therefore be advantageous to have a means to hasten the movement of a tooth or teeth so that the time period to move the tooth or teeth to a desired location is shortened.

Orthodontic cases are generally divided into two categories according to the direction the tooth movements are made, either expansion where crowded and crooked teeth are moved toward the periphery of the outline of the jawbone or retraction where one or more teeth are removed to create more room in the jaw. To align the teeth, one or more teeth may be moved in the direction of spaces created. Conventional orthodontics is performed by moving the root of a tooth through its surrounding bone in the jaw. The bone of the jaw has a hard outer shell, called the cortical plate or cortical bone, and a softer interior called the medullary bone.

The medullary bone has a good blood supply and is highly populated with pluripotential cells that can convert to osteoclasts that resorb old bone and osteoblasts that make new bone. Therefore, the medullary bone responds relatively dramatically and timely to physical insult including the forces used to move teeth. To move a tooth orthodontically, the root of the tooth must be moved through the bone surrounding the tooth, the alveolar bone consisting of the medullary bone and surrounding cortical plates that comprise the upper and lower jaws. The alveolar bone remodels around a tooth being moved in response to pressure and tension around the roots of teeth. In the course of such bone remodeling, bone resorption occurs on the pressure side of the root surface in the direction in which the tooth is moving. Bone deposition or new bone formation occurs on the tension side of the root surface in the direction away from which the tooth is being moved.

The root of a typical tooth is usually so large in diameter that it occupies most of the space between the lingual cortical plate on the inside of the jaw and the facial cortical plate on the outside of the jaw. As a result, much of the root of a tooth is covered with hard cortical plate and with very little soft medullary bone.

A major drawback to conventional orthodontics is the long treatment time during which braces must be worn. Corticotomy has been used for several decades to attempt to shorten orthodontic treatment times. The term refers to a bony cut or perforation that extends through the entire thickness of the cortical plate of the alveolus and into the underlying medullary bone or, if no medullary bone is present under the cortical plate, it refers to a bony cut or perforation that extends through most of the thickness of the cortical plate, but not its entire thickness.

Fischer et al., *Angle Orthod* 2007; 77:417-420 propose that instead of orthognatic surgery, small cuts be made in the alveolar bone around the teeth, a process that is known as corticotomy. It would be desirable if this highly invasive corticotomy procedure can be simplified even further and replaced with minimal, shallow, small perforations in alveolar bone without need for soft tissue flaps (as required with corticotomies).

Corticotomy has been used in difficult adult cases as an alternative to conventional orthodontic treatment or orthognathic surgery. It has been claimed that by combining a corticotomy procedure with orthodontics, it is possible to complete treatment in a shorter period of time due to the ability to move teeth more rapidly. The mechanism of this action is not clear. Several authors have described rapid tooth movement observed in conjunction with corticotomy as movement by "bony block." Based on this concept, a fissure is made through the cortical plate that surrounds a tooth, so that this tooth will now be in a block of bone connected to surrounding bone only through the medullary bone. The tooth is the "handle" by which this block of bone can be moved. Others have related the effect of corticotomy-facilitated orthodontics to the repair mechanism that is observed following injury of bone. After bone injury, accelerated bone turnover and decreases in regional bone density have been described.

Scott, U.S. Pat. No. 7,329,122 and Scott, U.S. Patent Publication No. 2008/0102415 teach using flapless corticotomy using long needles. This procedure requires fabrication of a guide to determine the best places for application of cortical perforations. Scott proposes using needles to produce deep and narrow perforations that may be damaging to tooth roots and surrounding tissues. To compensate for this side effect, Scott designed a complex template as a guide for safe application of multiple cortical plate perforations. This technology makes the application of these procedures very difficult and unpractical.

Wilcko et al., U.S. Pat. No. 6,109,916 teaches extensive cortical plate perforations requiring full thickness mucoperiosteal flap and bone grafting. These procedures are rather excessive to accelerate tooth movement. In addition they are extremely uncomfortable, time consuming, and expensive, involving different specialists. They also pose a significant risk for infection, rejection of bone graft, gingival recession, and bone loss. Some references describing this and similar procedures include for example, Yen S et al., *J Oral Maxillofac Surg* 61:1346-1350; 2003; Iino S et al., *Am J Orthod Dentofacial Orthop* 131: 448.e1-448.e8; 2007; Liou et al., *Am J Orthod Dentofacial Orthop* 117:391-8; 2000; Hwang et al., *Am J Orthod Dentofacial Orthop* 120:209-16; 2001; Germec D et al., *Angle Orthodontist* 76:882-890; 2006; Wilcko et al., *World J Orthod.* 4:197-205; 2003; Wilcko et al., *Int J Perio & Rest Dent.* 21: 9-19; 2001; and Fischer, *Angle Orthodontist.* 77-3; 2007.

Orthodontic forces induce an aseptic inflammatory response. During early stages of tooth movement, there is an increase in vascular permeability and cellular infiltration of leukocytes (Krishnan, et al., *Am J Orthod Dentofacial Orthop*, (2006a) 129:469.e1-469.e32; Meikle, *Eur J Orthod* (2006) 28:221-240). Migrated immune cells along with native cells such as fibroblasts and osteoblasts produce inflammatory cytokines which include lymphocyte- and monocyte-derived factors, colony-stimulating factors, growth factors, and chemotactic factors (Krishnan. et. al., *J Dent Res* (2009) 88(7):597-608; Ren, et al., *Eur J Oral Sci* (2008) 116(2):89-97). High concentrations of inflammatory cytokines such as interleukin-1 (IL-1), IL-2, IL-3, IL-6, IL-8, tumor necrosis factor-$\alpha$ (TNF$\alpha$), interferon-$\gamma$ (IFN$\gamma$,) and osteoclast differentiation factor have been found in the gingival crevicular fluid surrounding moving teeth (Alhashimi et al., *J Interferon Cytokine Res* (2000) 20(1):7-12; Garlet et al., *Eur J Oral Sci* (2007) 115(5):355-62; Ren et al., *J Periodontol* (2007) 78(3):453-8).

The role of cytokines during tooth movement is not very clear. It has been suggested that cytokines and other inflammatory markers such as prostaglandin E2 (Saito et al., *Am J Orthod Dentofacial Orthop* (1991) 99(3):226-40) may activate bone remodeling characterized by bone resorption in the compression region and bone deposition in the tension region of the periodontal ligament (PDL) (Davidovitch et al., *Dent Clin North Am* (1988) 32(3):411-35; Garlet et al., *Eur J Oral Sci* (2007) 115(5):355-62). This is in agreement with previous studies that demonstrated that bone injury which causes cytokine release, leads to an accelerated bone turnover and a decrease in regional bone density (Frost, *Henry Ford Hosp Med J* (1983) 31(1):3-9; Frost, Part II. *Clin Orthop Relat Res* (1989a) 248:294-309; Frost, Part I. *Clin Orthop Relat Res* (1989b) 248: 283-93; Shih, et al., *Bone* (1985) 6(5):377-9; Yaffe et al., *J Periodontol* (1994) 65(1):79-83). One possible mechanism through which inflammatory cytokines may affect bone remodeling is through recruitment of osteoclast precursors from the circulation, their maturation and activation. Many cytokines that promote osteoclast formation and activation, such as IL-1, IL-6, and TNF$\alpha$ (Glantschnig et al. *Cell Death Differ* (2003) 10(10):1165-77; Seidenberg, et al., *Pharmacol Res* (2004) 50(2):151-6; Yao et al., *J Biol Chem* (2008) 283(15):9917-24), have also been found in crevicular fluid during orthodontic tooth movement (Basaran et al., *Am J Orthod Dentofacial Orthop* 2006; 130:E1-6; Uematsu et al., *J Dent Res*. 1996; 75:562-567).

The effect of cytokine expression on bone remodeling is important since the rate of tooth movement correlates with the efficiency of bone remodeling in the alveolar process. Studies of knockout mice deficient for TNF$\alpha$ receptors (Yoshimatsu et al., *EJ Bone Miner Metab* (2006) 24(1):20-7) showed a slower rate of tooth movement in response to orthodontic forces. Also previous reports showed that anti-inflammatory medication can decrease the rate of tooth movement (Arias, et al., *Am J Orthod Dentofacial Orthop* (2006) 130(3):364-70).

It would be advantageous to provide methods and devices for assisting tooth movement that provide fewer number and lesser depth of perforations. Likewise, it would be advantageous to provide devices and kits that facilitate performing effective perforations so as to assist tooth movement without the disadvantages of conventional needles.

SUMMARY OF THE INVENTION

The present invention is based in part upon the discovery that limited and shallow perforations of the buccal cortical plate of the maxilla increase the expression of inflammatory cytokines, accelerate the bone remodeling process and therefore increase the rate of tooth movement. The present invention is also based in part upon the discovery that deep cortical perforations are not required to induce inflammation capable of accelerating tooth movement. The methods of the present invention do not require any template to prevent side effects associated with deep and narrow needles. The present invention is also based in part upon the discovery that the site of perforation is relatively unimportant to induce inflammation capable of accelerating tooth movement. In fact, the present invention demonstrates that both the site of perforation and the number of multiple perforations is relatively unimportant. Hence, the methods of the present invention are safer, more comfortable for the patient, present less risk of infection and require less recovery time.

In a first aspect, the present invention provides a method of moving a tooth to a desired positions within a patient's mouth comprising using osteoperforation-facilitated orthodontics. The method includes perforating or pricking tissue in the oral cavity sufficient to induce an inflammatory response in the tissue. An inflammatory response may be identified readily by the increased presence of certain cytokines such as certain interleukins or the increased presence of certain cells such as macrophages and monocytes as is well known in the art. The method further includes providing an orthodontic appliance on or near the tooth to be moved to exert force on the tooth toward the desired position. The orthodontic appliance may be installed on the tooth prior to or subsequent to the perforating or pricking, such as for instance, about one, two, three or four days or more, or one, two, three, four, five, ten or more weeks prior to or subsequent to the perforating or pricking. The methods may result in a reduction in the time required to move a tooth from a first position to a second position of at least about 5%, 10%, 20%, 25%, 30%, 40%, 50%, 60%, 75%, 80%, 90% or more as compared to the length of time required to move a tooth from a first position to a second position in instances where no perforations are provided.

If orthodontic appliances have not been installed prior to the perforations they can be installed after the perforations as desired. The orthodontic appliances, once activated, may be adjusted periodically, as needed, to move the teeth toward their desired positions. The methods of the present invention may be repeated as necessary to maintain a sufficient inflammatory response to expedite tooth movement. For instance, the methods may repeated daily, one, two, three, four or more times per week, or one, two, three, four, five, eight, ten, twelve, fifteen, twenty or more times per month. The orthodontic appliances must be adjusted frequently enough to complete the major orthodontic movements.

In one embodiment the method features making one or more shallow bone perforations in the tissue of the oral cavity. The perforations may be made, for instance, in any area of the maxilla or mandible. Preferably about 1 to 100, 1 to 50, 1 to 40, 1 to 25, 1 to 20, 1 to 15, 1 to 10, or 2, 3, 4, 5, 6, 7, 8 or more perforations are made in the tissue of the oral cavity. The perforations may be about 0.1 to 10 mm diameter, preferably 0.2 to 8 mm diameter, more preferably 0.3 to 7 mm diameter, 0.4 to 5 mm diameter, 0.5 to 3.0 mm diameter, or 1.0 to 1.5 mm diameter. The perforations may be about 0.5 to 15 mm deep, preferably 0.75 to 10 mm deep, and more preferably 1 to 8 mm deep, and still more preferably 3 to 6 mm deep. Preferably, the perforations do not penetrate the medullary bone. Such perforations are sufficient to enhance the bone remodeling process and subsequently accelerate tooth movement. In some embodiments, the perforations are made using the devices and kits described herein. In some embodiments, a shallower perforation of, for instance, 1-2 mm may be placed in thinner bone such as the bone closer to alveolar crest while deeper perforations, for instance, greater than 3 mm in depth may be placed in thicker bone such as the bone closer to the middle or apical part of the roots. In some instances, a pilot drill or soft tissue punch may be necessary. In some embodiments, 2 or 3 perforations medial and distal of the tooth or teeth that are to be moved is enough. The perforations may be placed about 1 to 5 mm or 2 to 3 mm from the alveolar crest. Further, the perforations may be placed about 0.1 to 10 mm, 0.5 to 5 mm or 1 to 2 mm distance from each other. The perforations may be placed in attached gingiva areas for simplicity and reduction of discomfort. In some instances, in areas where, for instance due to dense bone or difficult location of tooth, direct application of a hand instrument is difficult or impossible, perforations may be made using a relatively slow speed handpiece having burs. The burs preferably also have markers to show different depths. After the perforations are made, a gauze may be placed in the area of the perforations for a period of time, such as 1-10, 2-6 or 3-4 minutes. Following the perforations, the patient may use a chemical antiseptic such as, for example, Peridex, for a few days or a week or two weeks after the perforations. In many instances, other medication is not necessary unless the systemic health of the patient necessitates.

In another embodiment the method features performing osteoperforations by rinsing the oral cavity with a chemical antiseptic such as, for example, Peridex, applying a local anesthetic such as lidocaine 2% or carbocaine and making small perforations having a bone depth of preferably about 0.5 to 10 mm, 0.75 to 5 mm or 1-3 mm. The perforations may be made, for instance, in any area of the maxilla and mandible. Preferably about 1 to 100, 1 to 50, 1 to 40, 1 to 25, 1 to 20, 1 to 15, 1 to 10, or 2, 3, 4, 5, 6, 7, 8 or more perforations are made in the tissue of the oral cavity. The perforations may be about 0.1 to 10 mm diameter, preferably 0.2 to 8 mm diameter, more preferably 0.3 to 5 mm diameter, 0.4 to 3 mm diameter or 0.5 to 1.5 mm diameter. The perforations may be placed using a hand instrument such as a hand drill. Preferably, the hand drill has markers or stops that show depths. In some embodiments, a shallower perforation of, for instance, 1-2 mm may be placed in thinner bone such as the bone closer to alveolar crest while deeper perforations, for instance, greater than 3 mm in depth may be placed in thicker bone such as the bone closer to the middle or apical part of the roots. In some instances, a pilot drill or soft tissue punch may be necessary. In some embodiments, 2 or 3 perforations medial and distal of the tooth or teeth that are to be moved are enough. The perforations may be placed about 1 to 5 mm or 2 to 3 mm from the alveolar crest. Further, the perforations may be placed about 0.1 to 10 mm, 0.5 to 5 mm or 1 to 2 mm distance from each other. The perforations may be placed in attached gingiva areas for simplicity and reduction of discomfort. In some instances, in areas where, for instance due to dense bone or difficult location of tooth, direct application of a hand instrument is difficult or impossible, perforations may be made using a relatively slow speed handpiece having burs. The burs preferably also have markers or stops to show different depths. After the perforations are made, a gauze may be placed in the area of the perforations for a period of time, such as about 1-10, 2-6 or 3-4 minutes. Following the perforations, the patient may use a chemical antiseptic such as, for example, Peridex, for a few days or a week or two weeks after the perforations. In many instances, other medication is not necessary unless the systemic health of the patient necessitates. In some embodiments, the osteoperforations are performed near to or as close as possible to the time of tooth movement. In some embodiments, the osteoperforations are performed after adjusting an orthodontic appliance.

In some embodiments, the perforations are made sufficient in number and sufficient in size to increase the expression of one or more inflammatory markers in tissue near to, proximate to, or even distal from the tooth to be moved or in tissue near to, proximate to, or even distal from the tissue in which the perforations are made. The subject tissue may be for instance, within about 1 mm of the tooth to be moved, or the subject tissue may be within 2 mm, 3 mm, 4 mm, 5 mm, 6 mm, 8 mm, 10 mm, 12 mm, 15 mm or 20 mm or even farther from the tooth to be moved. The expression of the one or more inflammatory markers may be increased by about 10%, 20%, 25%, 30%, 40%, 50%, 60%, 75%, 80%, 90%, 100%, 125%, 150%, or even by two fold, three fold, four fold, five fold, ten fold or more as compared to the expression of the one or more inflammatory markers prior to any perforations. The increase in the expression of the one or more inflammatory markers may be measured at any time after the first perforation is performed, such as, for instance, about 1 hour, 3 hours, 6 hours, 12 hours, 18 hours, 24 hours, 36 hours, 48 hours, 72 hours, or even 4, 5, 6, 7, 10, 12, 14, or 21 days after the first perforation is made. The one or more inflammatory markers may be, for instance, one or more cytokines, one or more chemokines, or one or more inflammatory receptors. The one or more inflammatory markers may be, for instance, one or more of markers of lymphocytes such as CCL20 or CCR1, one or more markers of T cells such as LTa, IL-3, CCL5, CCR5, CX3CR1, IL-18rb, or IL-1r1, one or more markers of monocytes such as IL-1, IL-6, Il11, IL-18, or IL-6ra, or one or more markers of macrophages such as IL-1, TNF, IL-6, IL-18, IL13ra1, CCL2, CCL9, CCL12, CCR5, or IL-6ra. In still other embodiments, the perforations are made sufficient in number and sufficient in size to increase osteoclast activity on the surface of bone near the tooth to be moved, such as, for instance the alveolar bone surface. Such osteoclast activity may be measured by any known methods such as for instance, identification of the number of TRAP-positive (tartrate-resistant acidic phosphatase) osteoclasts. In some instances, the number of TRAP-positive osteoclasts may be increased by about 10%, 20%, 25%, 30%, 40%, 50%, 60%, 75%, 80%, 90%, 100%, 125%, 150%, or even by two fold, three fold, four fold, five fold, ten fold or more as compared to the number of TRAP-positive osteoclasts prior to any perforations. The increase in the number of TRAP-positive osteoclasts may be measured at any time after the first perforation is performed, such as, for instance, about 15 minutes, 30 minutes, 1 hour, 2 hours, 3 hours, 4 hours, 6 hours, 12 hours, 18 hours, 24 hours, 36 hours, 48 hours, 72 hours, or even 4, 5, 6, 7, 10, 12, 14, or 21 days after the first perforation is made.

In a second aspect, the present invention features a device for osteoperforation, that is, a device for making minute perforations in bone such as the alveolar bone. The shallow perforations that may be, for instance, about 2-6 mm in length and 1 to 2 mm in width may be made through the gum into alveolar bone in areas adjacent to the teeth. The depth and width of the perforations are controlled by the present invention and the number of perforations. The number of perforations can range from one to multiple perforations depending on the bone density. In areas where the bone is denser, more perforations may be necessary. The device may be, for instance, a hand held device such as a hand held drill as described herein.

In a third aspect, the present invention features a kit containing the device of the present invention. That is, the kit contains one or more of the necessary components that can be used by a dentist or orthodontist to readily and conveniently perform the methods of the present invention and speed the movement of a tooth to a new, desired position. The kit may contain, for instance, a hand device such as a hand drill, as described herein. The kit may further contain, for instance, instructions for operating the hand device or hand drill or instructions for making the desired perforations.

BRIEF DESCRIPTION OF THE FIGURES

FIG. 1 demonstrates that osteoperforations increased the rate of tooth movement. (A) Photograph with schematic overlay showing the three shallow perforations (0.25 mm diameter) created 4 mm mesial to the first molar. (B) Schematic showing the three shallow perforations (0.25 mm diameter and depth) created, 5 mm mesial to the first molar. (C) Representative photographs of rat maxillae showing movement of upper left first molar at 28 days in the four groups. C, control; O, orthodontic force alone; OF, orthodontic force plus flap; OFP, orthodontic force plus flap plus perforations. Original magnification 15×.

FIG. 5 demonstrates that osteoperforations induced osteopenia in the entire length of alveolar bone. Mean maxillary bone volume fraction (BV/TV %) of the four groups at 28 days posttreatment. (A) Schematic overlay indicating axial sections (1, 2, 3) and coronal sections (a, b, c) used in the analysis. (B) Mean bone volume fraction in each of the nine zones in the four groups, derived from microCT data. Note increase in trabecular spacing, indicative of bone remodeling activity, in the OFP group. C, control; O, orthodontic force alone; OF, orthodontic force plus flap; OFP, orthodontic force plus flap plus perforations. *Significantly different from C, $p<0.05$; **Significantly different from C, O, and OF, $p<0.05$.

FIG. 9A illustrates a disposable hand held perforating device. FIG. 9B illustrates a modified version of a hand perforating device that has an abbreviated handle. FIG. 9C shows a disposable package. FIG. 9D illustrates a disposable package having a container body and a removable cover;

FIG. 11A shows a normal alveolar bone. FIG. 11B shows the alveolar bone and gum perforated. FIGS. 11C and 11D demonstrate the steps in using a rotating perforating device.

DESCRIPTION OF THE PREFERRED EMBODIMENTS

Figure 2A:
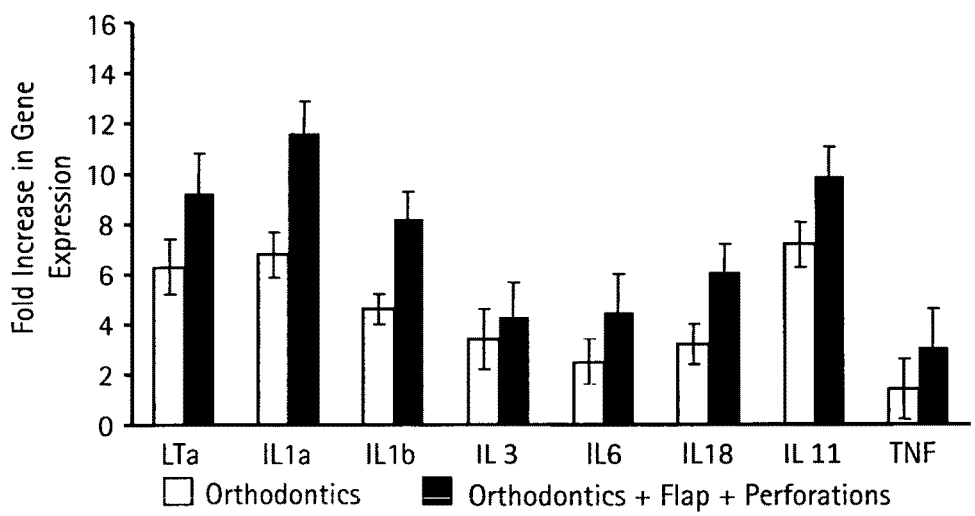
FIG. 2 demonstrates that osteoperforations increase expression of inflammatory markers. Mean "-fold" increase in expression of cytokines (A), chemokines (B), and inflammatory receptors (C) in the orthodontic group (O, white bars) and the orthodontic force plus flap plus perforations group (OFP, black bars) compared to controls. All values shown, except for TNF in the orthodontic (O) group, showed a statistically significant increase when compared to control. *Significantly different from orthodontic (O) group, $p<0.05$.

The present methods apply biological principles to clinical orthodontic treatment. Previously, to accelerate tooth movement procedures such as corticotomy and osteotomy were used with the purpose of weakening the bone through extensive and traumatic bone cuts after large soft tissue flap in hope of moving a tooth with bone blocks. This "bone weakening" has been referred to as Regional Accelerated Phenomenon. The present methods recognize that the increase in bone remodeling and consequent tooth movement is not dependent on the extensive cutting or mechanical weakening of bone but on the stimulation of an inflammatory reaction. The present methods provide a minimally traumatic procedure that still elicits the inflammatory reaction, resulting in bone remodeling and accelerated tooth movement. The present methods further provide increasing the rate of tooth movement to reduce the overall orthodontic treatment duration, while extending the range of tooth movement. The present methods are less invasive, less traumatic and pose no or only minimal risks for the patient. Therefore, the present methods may be safely performed by any orthodontist and does not require the services of a periodontist or a surgeon.

The present methods are to be used in combination with orthodontic appliances when there is need for increased range of tooth movement due to severe skeletal discrepancies. The present methods provide a simple and novel approach for clinicians to perform osteoperforations to induce accelerated bone remodeling. The present methods are atraumatic without gingival flap, with minimum discomfort performed in a relatively short period of time with minimal side effects. These methods allow accelerated tooth movement in a short period of time in any direction, expanding the range of tooth movement to such an extent that was only possible previously through orthognatic surgery. Due to accelerated bone remodeling, tooth movement in areas that previously were not possible such as atrophic bone, become feasible. While the methods are mostly designed for a flapless approach, if they are combined with flap design and bone grafting techniques they may further extend the range of tooth movement and bone formation beyond the flapless approach, limiting the usage of expensive and traumatic orthognatic surgery and making the treatment affordable and accessible to public.

A stand alone device that may be used in conjunction with slow-speed rotary instruments or may also be utilized with manual drivers is also provided. The device may provide one or more of the following: a gingival tissue hole-punch; a high quality disposable (e.g. tungsten-carbide/surgical steel) depth limiting burs with a diameter of 1 to 2 mm, and cutting length of for instance, 1, 2, 3, 4, 6, 8 and 10 mm with safe stops, and smooth cuff to prevent damage to soft tissue. Burs may be utilized either with low speed rotary or manual drivers. The device may further feature a manual driver capable of engaging and releasing burs.

Referring now to FIGS. 9A-9D, there is shown a disposable hand held perforating device 10 constructed in accordance with the present invention and a disposable package that may be used to contain the hand held perforating device 10. The hand held perforating device 10 is comprised of a handle 12 for holding by the user and a shaft 14 extending therefrom. The shaft 14 has a distal end 16 and a small drill 17. There is a stop 18 displaced a predetermined distance inwardly from the distal end 16. The handle 12 of device may be comprised of plastic while the small drill 17 may be made of metal (preferably titanium). The perforating device 10 may be provided in different lengths or widths. The predetermined length of the small drill 17, in the exemplary embodiment, can be 6, 8 or 10 mm while the thickness or diameter may be between 1.5 or 2 mm, however other lengths and diameters can be used. The hand held perforating device 10 may be used to make perforations in the alveolar bone, as will be described with respect to FIGS. 11A-11C, of a known, predetermined diameter and depth.

Figure 9A:
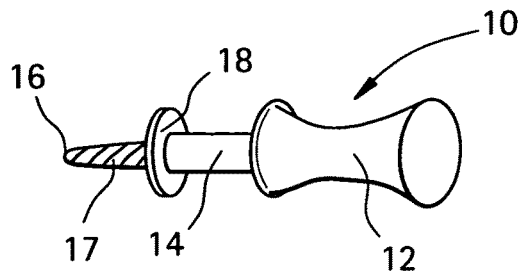
FIGS. 9A-9D are schematic views of a hand held perforating device along with a disposable container usable to contain the same.
Figure 9B:
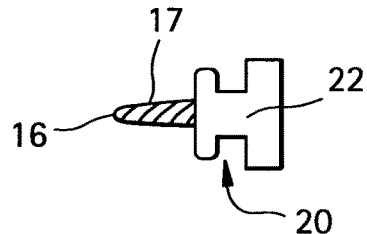

In FIG. 9B, there is depicted a modified version of a hand perforating device 20 that has an abbreviated handle 22 that may be used to make perforations in the aleveolar bone of a patient in areas that cannot be accessed by the hand perforating device 10 of FIG. 9A such as areas of posterior teeth (second molars), or where the patient cannot fully open the mouth. This modified version of a hand held perforating device 20 may also be provided in different lengths and widths of the small drill 17.

Figure 9C:
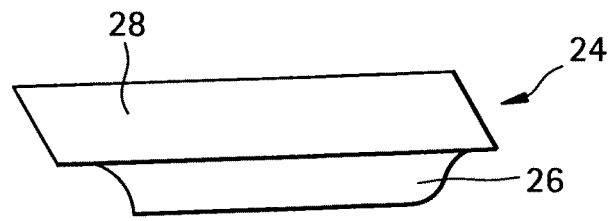
Figure 9D:
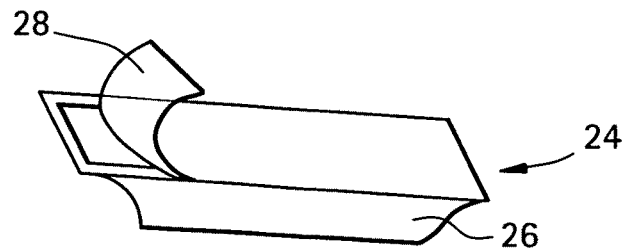

The hand held perforating devices 10 and 20 can be provided to the user in a disposable package as shown in FIG. 9C. As seen in FIG. 9C, there is a sealed container 24 that can contain a hand held perforation device 10 or 20 in a sterilized format for one time usage. This package has a container body 26 and a removable cover 28. In FIG. 9D, it can be seen that the cover 28 has been partially peeled back for access to the components contained within the container body 26.

Figure 10:
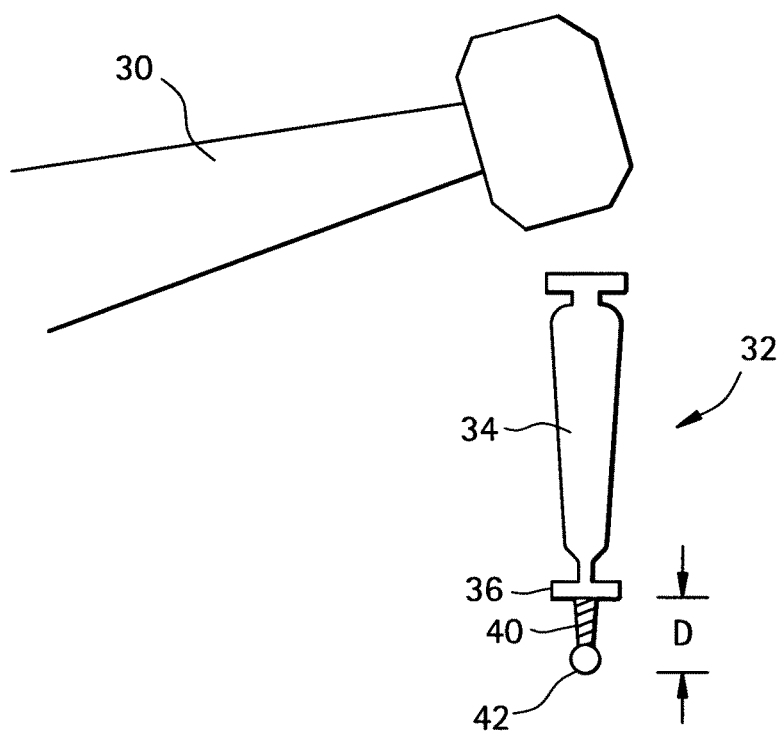
FIG. 10 is a schematic view of a rotatory perforating device that can be attached to a dental hand piece.

In FIG. 10, there is illustrated a slow speed dental handpiece 30 or other instrument having a rotating chuck attachable to a perforating device 32 of the present invention. The means of attachment may be conventional with such dental handpieces such that that the perforating device 32 may be rotated at a relatively slow speed. As can be seen, the perforating device 32 has a circular shaft 34 and at the end of the shaft 34 is a small drill 40 with a cutting end. A stop 36 is located on the shaft 34 at predetermined linear distance inwardly of a distal tip 42 of the small drill 40 to stop the small drill 40 from penetrating the alveolar bone more than a predetermined depth. The small drill 40 may be provided in different lengths and widths of diameters, such as a length D of 4 or 6 mm and a width or diameter of 1.5 mm or 2 mm.

Figure 11A:
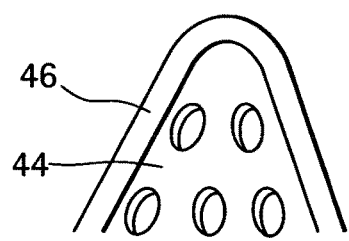
FIGS. 11A-11D are schematic views illustrating the use of the present devices to perform osteoperforation.

Turning now to FIG. 11A-11D, there is shown schematic views illustrating the use of the devices of the present invention. In FIG. 11A, a normal alveolar bone 44 is illustrated. The alveolar bone 44 is part of the jaw bone that accommodates the teeth and which is covered by the gum 46 or gingiva.

Figure 11B:
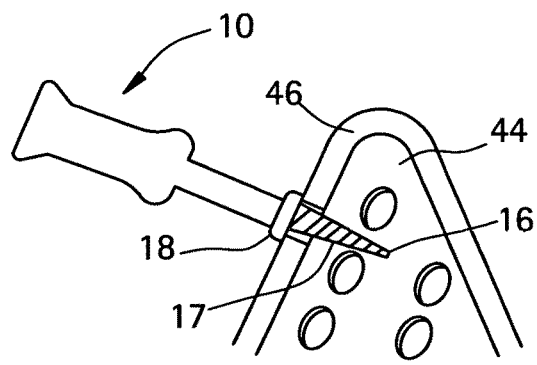

Turning to FIG. 11B, there is shown the alveolar bone 44 and gum 46 has been perforated directly by hand held perforating device 10 as described with respect to FIG. 9A. Stop 18 determines the depth of penetration of the perforation that the hand held perforating device 10 will produce inside the bone.

Figure 11C:
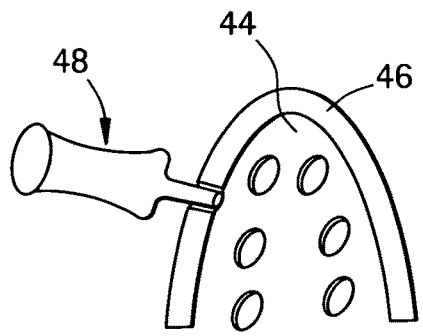
Figure 11D:
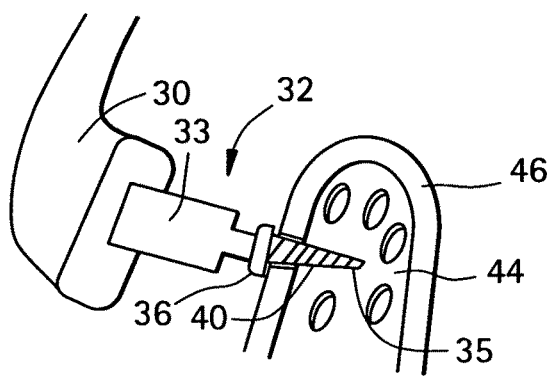

FIGS. 11C and 11D demonstrate the steps in using a rotating perforating device 32 that is attached to the dental handpiece 30. As before with a hand held device, the rotating perforating device 32 has a shaft 33 having a distal end 35 and a small drill 40. As stop 36 is also provided to function as a limiter to the depth of penetration of the small drill 40.

While it is not mandatory, it is may be preferable in certain cases that a soft tissue punch 48 be used before application of a rotating device, see FIG. 11C, especially in places where gum tissue is loose. Application of the soft tissue punch 48 with a rotating perforating device 32 may prevent damage to gum. The soft tissue punch 48 can create an opening in the gums of the patient so that the later use of a rotating perforation device 32 does not catch up in the gum tissue with the drill 40 so that the drill 40 enters cleanly into the bone 44. In areas where the gum is firmly attached to the bone 44, application of soft tissue punch 48 may not be necessary. Following punching of the soft gum tissue, the rotating perforating device 32 can directly access the bone 44 as illustrated in FIG. 11D.

The device may be provided in a kit. The kit may also contain one or more of a disposable local anesthetic carpule, and topical analgesic swabs, a depth gauge probe, and an illustrated detailed instruction manual.

Figure 12:
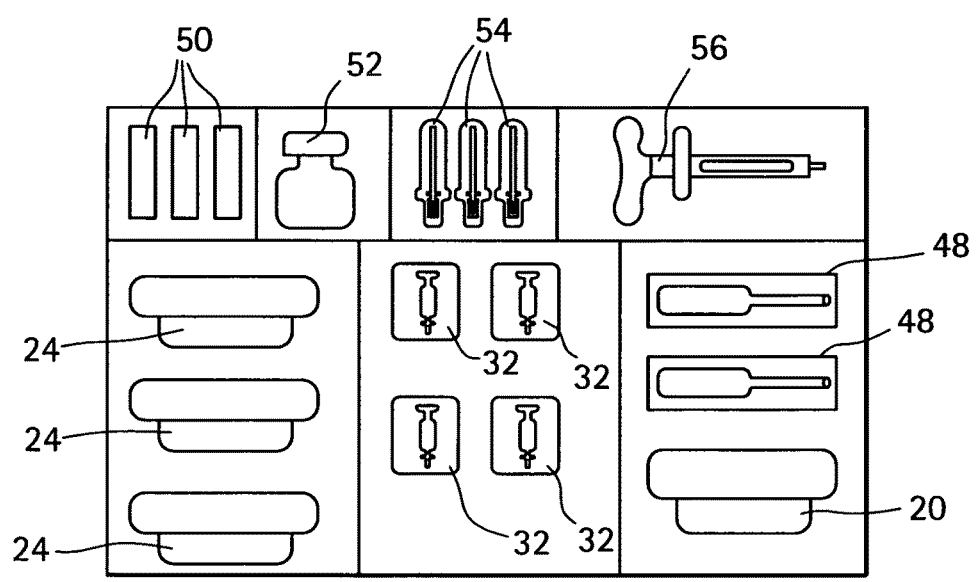
FIG. 12 illustrates the components that can be incorporated into a kit to perform osteoperforation.

FIG. 12 demonstrates an inventive kit form that can be conveniently used for performing the methods of this invention. It is envisioned that the present kit can be supplied to dentists or orthodontists so that the doctor will have all of the components necessary to carry out the osteoperforation method of the present invention. This kit includes a container having therein a local anesthetic 50 (lidocaine HCL 2%), a topical anesthetic 52, a syringe for application of local anesthetic 56, short needles 54, soft tissue punch 48 and different length and widths of hand held perforating devices in disposable packages 24, short modification of hand perforating devices for access to difficult area in disposable packages 20 and different length and widths of small drills for application with dental handpiece 32. As can be seen, one or more of the previously listed components may be omitted in a particular kit. The kit may be contained in a disposable container similar, but different in dimensions, to that described with respect to FIGS. 9C and 9D.

As described elsewhere herein, the procedure may include the following steps: first, a topical anesthetic is applied in the desired area, followed by local anesthetic injection using a syringe and short needle. The anesthetic is used to deaden the tissue where the perforation is to be made. In majority of cases, using one standard hand held perforating device should be adequate, but if the patient has very dense alveolar bone, a strong device such as rotatory perforating device attached to dental handpiece will be helpful. In such cases, a disposable punch 48 can be used to facilitate the procedure.

Those skilled in the art will readily recognize numerous adaptations and modifications which can be made to the devices used to carry out that method with will result in improved devices, yet all of which will fall within the scope and spirit of the present invention as defined in the following claims. Accordingly, the invention is to be limited only by the following claims and their equivalents.

SUMMARY

It is unclear whether corticotomy facilitates orthodontic tooth movement by reducing physical constraints or via a mechanism resembling that in bone response to injury. Since inflammation is an underlying mechanism, it is preferable to administer the minimal injury capable of eliciting an inflammatory response. Forty-eight rats were fitted with closing coils and subjected to either a 50 cN force to the maxillary first molar (O), the same force after implementation of a soft tissue flap (OF), force plus flap plus three perforations of the cortical plate mesial to the first molar (OFP), or no force (controls: C). Perforations of cortical bone resulted in increased inflammatory reaction as shown by RT-PCR of RNA at 24 h. At 28 days post-treatment, micro-computed tomography, light and fluorescent microscopy, and immunohistochemistry revealed increased rates of tooth movement and bone remodeling. The increase in rate of bone remodeling extended beyond the first molar region to the adjacent alveolar bone. Shallow perforations of cortical bone are sufficient to stimulate an inflammatory response capable of accelerating bone remodeling and tooth movement. The procedure is easy to perform, minimizes side effects and discomfort, and shortens recovery time.

Corticotomy is sometimes used in difficult adult cases as an alternative to conventional orthodontic treatment or orthognathic surgery. (Kole, *Oral Surg Oral Med Oral Pathol* 1959; 12:515-529; Anholm, et al., *CDA J* 1986; 14:7-11; Gantes, et al. *J Periodontol* 1990; 61:234-238; Wilcko, et al., *Int J Periodontics Restorative Dent* 2001; 21:9-19; Chung, et al., *J Clin Orthod* 2001; 35:331-339) The ability to move teeth more rapidly, it is claimed, makes it possible to complete treatment in a shorter period of time. The mechanism of this action is not clear. Several authors have described rapid tooth movement observed in conjunction with corticotomy as movement by "bony block." (Kole, *Oral Surg Oral Med Oral Pathol* 1959; 12:515-529; Anholm, et al., *CDA J* 1986; 14:7-11) The practitioner creates a fissure through the cortical plate surrounding the tooth, in effect making the tooth a block of bone connected to surrounding bone only through the medullary bone. The tooth is thus a "handle" by which this block of bone can be moved. Others have compared the effect of corticotomy-facilitated orthodontics to the repair mechanism that is observed following injury of bone. (Wilcko, et al., *Int J Periodontics Restorative Dent* 2001; 21:9-19) After bone injury, accelerated bone turnover and a decrease in regional bone density have been described. (Frost, *Henry Ford Hosp Med J* 1983; 31:3-9; Frost, *Clin Orthop Relat Res* 1989: 294-309; Frost, *Clin Orthop Relat Res* 1989; 283-293; Yaffe; et al. *J Periodontol* 1994; 65:79-83) While the mechanism of this accelerated bone turnover is not completely understood, it is reasonable to hypothesize that inflammation plays an important role.

Inflammation can alter the physiology and structure of bone by modifying the normal pattern of remodeling through stimulation of bone resorption and formation. The inflammatory process can affect the recruitment of osteoclast precursors from the circulation, including their rate of maturation and their level of activity. Many cytokines that promote osteoclast formation and activation, such as IL-1, IL-6, and TNFα, are abundantly synthesized by inflammatory cells. (Seidenberg, et al., *Pharmacol Res* 2004; 50:151-156; Glantschnig, et al., *Cell Death Differ* 2003; 10:1165-1177; Bolander, *Proc Soc Exp Biol Med* 1992; 200:165-170; Busti, et al., *Pharmacotherapy* 2005; 25:1566-1591) These cytokines may thus be central to the biological response in accelerated tooth movement during corticotomy.

Understanding the mechanism by which corticotomy can facilitate orthodontics tooth movement is important because the surgical design of corticotomies has been greatly influenced by clinicians' mechanistic view of the underlying biological process. If the purpose of corticotomy is to weaken the bone around the tooth, then the surgery should be designed to create a loose block of bone around the tooth to be moved. If, however, the goal of the corticotomy is to accelerate the bone remodeling process by evoking an inflammatory response, then the geometry of the surgical cuts is not so crucial, and the minimal injury that activates the bone repair system would suffice requiring less traumatic surgical design. The current study demonstrates that limited shallow perforations of the buccal cortical plate of the maxilla are sufficient to accelerate the bone remodeling process and therefore tooth movement.

While there are many case reports of the ability of corticotomy to accelerate tooth movement, the biological principle underlying this phenomenon has been previously unclear. We used a rat model and created three shallow cortical perforations, mesial to the first molar, to elicit an inflammatory response. The rat is considered a good experimental animal model for the study of bone biology and physiology. (Frost, *Henry Ford Hosp Med Bull* 1965; 13:161-172; Tran, *J Pharmacol* 1982; 13:495-499; Vignery, et al., *Anat Rec* 1980; 196:191-200.) The biomechanical system used in this study to apply orthodontic force to the molar is also well established. (King, et al., *Am J Orthod Dentofacial Orthop* 1991; 99:456-465; Williams, et al., *Biomaterials* 1984; 5:347-351)

The demonstration that inflammation is the key player in controlling rate of tooth movement is based in part on the observation that application of antiinflammatory drugs can reduce tooth movement. (Arias, et al., *Am J Orthod Dentofacial Orthop* 2006; 130:364-370; Chao, et al., *Acta Anat (Basel)* 1988; 132:304-309) Additionally, studies of knockout mice deficient in IL-1 and TNFα receptors showed a slower rate of tooth movement in response to orthodontic forces. (Kitaura, et al., *J Dent Res* 2008; 87:396-400; Jager, et al., *Eur J Orthod* 2005; 27:1-11) These observations are also in harmony with studies showing that application of orthodontic force, regardless of magnitude, can stimulate an inflammatory response. (Arias, et al., *Am J Orthod Dentofacial Orthop* 2006; 130:364-370; Chao, et al., *Acta Anat (Basel)* 1988; 132:304-309; Kitaura, et al., *J Dent Res* 2008; 87:396-400; Krishnan, et al., *Am Orthod Dentofacial Orthop* 2006; 129:469 e461-432; Iino, et al., *Am J Orthod Dentofacial Orthop* 2007; 131:448 e441-448; Garlet, et al. *Eur J Oral Sci* 2007; 115:355-362; Kawasaki, et al., *Orthod Craniofac Res* 2006; 9:137-142; Ren, et al., *J Periodontol* 2007; 78:453-458; Mermut, et al., *Angle Orthod* 2007; 77:135-141) During early stages of tooth movement, there is an initial inflammatory response phase, evidenced by an increase in vascular permeability and cellular infiltration of lymphocytes, monocytes, and macrophages. (Rygh, et al., *Am J Orthod* 1986; 89:453-468) High concentrations of inflammatory cytokines such as IL-1, IL-2, IL-3, IL-6, IL-8, TNFα, IFNγ, and osteoclast differentiation factor (ODF) have been found in the gingival crevicular fluid surrounding moving teeth. (Garlet, et al., *Eur J Oral Sci* 2007; 115:355-362; Kawasaki, et al., *Orthod Craniofac Res* 2006; 9:137-142; Ren, et al., *J Periodontol* 2007; 78:453-458; Mermut, et al. *Angle Orthod* 2007; 77:135-141, Alhashimi, et al., *J Interferon Cytokine Res* 2000; 20:7-12)

The present data demonstrates that limited and shallow perforations of the cortical bone can significantly increase the inflammatory response. Increase in inflammation was demonstrated not only at the histological level by vascular invasion and infiltration of inflammatory cells, but also at the gene level by a significant increase in the expression of several cytokines and their receptors. Indeed, markers of lymphocytes (CCL20, CCR1 (Kao, et al., *J Immunol* 2005; 175:6676-6685; Sallusto, et al., *J Exp Med* 1998; 187:875-883; Han, et al., *Glia* 2000; 30:1-10)), T cells (LFa, IL-3, CCL5, CCR5, CX3CR1, IL-18rb, IL-1r1 (Schneider, et al., *Immunol Rev* 2004; 202:49-66; Khapli, et al., *J Immunol* 2003; 171:142-151; Xu, et al., *Ann Acad Med Singapore* 2007; 36:91-95; Ito, et al. *J Immunol* 1999; 162:4260-4265; Lean, et al. *J Cell Biochem* 2002; 87:386-393)), monocytes IL-6, Il11, IL-18, IL-6ra (Arend, et al., *Immunol Rev* 2008; 223:20-38; Adachi, et al., *Biol Pharm Bull* 1994; 17:1554-1560; de Sa A R, et al., *Oral Surg Oral Med Oral Pathol Oral Radiol Endod* 2003; 96:356-360; Dienz, et al., *Clin Immunol* 2009; 130:27-33; Bai, et al., *Tissue Antigens* 2007; 70:390-397; Bossu, et al. *J Neurol Neurosurg Psychiatry* 2007; 78:807-811; Jang, et al. *Clin Exp Rheumatol* 2005; 23:S59-63; Lean, et al., *J Cell Biochem* 2002; 87:386-393; Knupfer, et al., *Immunol Cell Biol* 2008; 86:87-91; Yamamoto, et al., *J Periodontal Res* 2006; 41:554-559; Leng, et al., *Int J Biochem Cell Biol* 1997; 29:1059-1062)), and macrophages (IL-1, IL-6, IL-18, CCL9, CCL12, CCR5, IL-6ra (Arend, et al., *Immunol Rev* 2008; 223:20-38; Adachi, et al. *Biol Pharm Bull* 1994; 17:1554-1560; de Sa A R, et al., *Oral Surg Oral Med Oral Pathol Oral Radiol Endod* 2003; 96:356-360; Bai, et al., *Tissue Antigens* 2007; 70:390-397; Yamamoto, et al., *J Periodontal Res* 2006; 41:554-559; Leng, et al., *Int J Biochem Cell Biol* 1997; 29:1059-1062; Hinton, et al., *Am J Orthod* 1986; 89:492-498)) were all found elevated in the OFP group in comparison to the 0 group 24 h after initiation of the experiment, suggesting substantial differences in the inflammatory response. In addition, a significant increase in both CCL2 (monocyte chemoattractant protein-1 (Piemonti, et al., *Diabetes* 2002; 51:55-65)) and CCR2 (receptor for CCL2 (Luster, *N Engl J Med* 1998; 338:436-445; Shireman, *J Vasc Surg* 2007; 45 Suppl A:A48-56))—produced and expressed in endothelial cells, vascular smooth muscle cells, tubular epithelial cells, lymphocytes, and monocyte/macrophages (Piemonti, et al., *Diabetes* 2002; 51:55-65)—confirm the extensive and massive vascular invasion observed in the OFP group.

The discovery that an increase in inflammation through minimal bone perforations accelerated the rate of bone remodeling is in agreement with previous reports that an increase in inflammation during bone injury is accompanied by an accelerated rate of bone remodeling. (Frost, *Henry Ford Hosp Med J* 1983; 31:3-9; Frost, *Clin Orthop Relat Res* 1989; 294-309; Frost, *Clin Orthop Relat Res* 1989; 283-293; Yaffe, et al., *J Periodontol* 1994; 65:79-83; Shih, et al., *Bone* 1985; 6:377-379. The present data demonstrate that the increase in bone remodeling rate is not limited to the area of the loaded tooth, but extends to the tissues surrounding adjacent teeth. This generalized increase in bone turnover was accompanied by osteopenia, as reflected by a decrease in bone density of the entire hemimaxilla.

Higher level of expression of cytokines and their receptors is important, since it has been shown that inflammatory cytokines play an important role in recruitment of osteoclasts and activation of the bone remodeling machinery (Alhashimi et al., *J Interferon Cytokine Res* (2000) 20(1):7-12; Krishnan, et al., *J Dent Res* (2009) 88(7):597-608; Ren, et al., *Eur J Oral Sci* (2008) 116(2):89-97). The fact, that the number of osteoclasts and the bone remodeling rate was higher in OFP group in comparison with O and OF group, supports the possible role of inflammatory cytokines in recruiting osteoclasts into the area.

Similar to previous studies (Verna et al., *Bone* (1999) 24(4):371-9), the present data demonstrate that the increase in bone remodeling rate is not limited to the area of the loaded tooth, but extends to the tissues surrounding adjacent teeth. This generalized increase in bone turnover is accompanied by osteoporosis, as reflected by a decrease in bone density around all upper left molars. While a limited number of osteoperforations have a generalized effect, the effect is not robust enough to cross to the contra-lateral side.

Since bone remodeling controls the rate of tooth movement, the increase in rate of bone remodeling and osteopenia in response to bone perforations may explain the increase in rate and magnitude of tooth movement demonstrated by these data. Our results further indicate that the site of the perforations that set this process in motion may not need to be in the vicinity of the tooth to be moved.

The present results were obtained using perforations that were very small and limited (only 3). Therefore the majority of the cortical bone remained intact. In addition, the perforations were placed far away from the tooth, and could still be observed at the end of the study with remaining bone (about 4 mm) between perforations and the moved tooth. These results further suggest that the perforations do not need to be in the close vicinity of the tooth to be moved in order to accelerate the rate of movement.

Inflammation can be beneficial by accelerating bone remodeling and tooth movement, however, if uncontrolled it may also have a destructive effect on the periodontium and tooth structure. Root resorption may be affected by osteoperforation. While extensive injury to the cortical plate bone, also referred to as corticotomies, is currently being used to accelerate orthodontic tooth movement in private practice, the present data indicate that this approach could be simplified to minimize deleterious side effects. Therefore, flapless minimal cortical perforations may be used as a means of fine tuning inflammation levels for enhanced tooth movement, enabling orthodontists to provide more efficient treatment to their patients.

Understanding the biological principles of corticotomy not only facilitates simplifying the procedure making it more practical for clinicians to employ, but also offers other possibilities. If inducing injury accelerates bone remodeling, then extraction of teeth should have a similar effect. Orthodontists may schedule extractions that are part of the treatment plan close to the time of major tooth movement. It is also important to observe that inflammation is a two-edged sword—that while it can work to the benefit by accelerating bone remodeling and tooth movement, it may also, if uncontrolled, exert a destructive effect on the periodontium.

Orthodontic Method

Orthodontic appliances are installed on the teeth to be moved to exert force on the teeth toward the desired positions. Any orthodontic appliances or auxiliaries either fixed or removable, installed on teeth may be used in accordance with this invention, and for any orthodontic, orthopedic or surgical purpose.

The basic principles of the orthodontic method of this invention are applicable in retraction cases and expansion cases. Retraction cases may also require that teeth be expanded, as well, as indicated above. Additionally, since retraction cases normally require the extraction of teeth and move teeth in the opposite direction from the movement of teeth in expansion cases, retraction cases are handled somewhat differently. The retraction devices used in the present methods may be constructed out of components and materials used by those skilled in the art to construct orthodontic palatal expansion devices such as shown in U.S. Pat. No. 4,347,054 Kraus et al., U.S. Pat. No. 4,354,832, Wallshein, U.S. Pat. No. 4,433,956, Witzig, U.S. Pat. No. 4,482,318, Forster, U.S. Pat. No. 5,281,133, Farzin-Nia, U.S. Pat. No. 5,002,485, Aagesen, U.S. Pat. No. 5,439,377, Milanovich, U.S. Pat. No. 5,472,344, and Binder et al. U.S. Pat. No. 4,483,674. The design and nature of fixed rapid palatal expanders are discussed by Anthony Viazis entitled Atlas of Orthodontics: Principles and Clinical Applications, published by W. B. Saunders Company, pp. 205-13, 1993 and by James A. McNamara, et al., entitled Orthodontic and Orthopedic Treatment in the Mixed Dentition, published by Needham Press, pp. 131-44, 1993. The design and nature of removable expanders are described by T. D. Foster entitled A Textbook of Orthodontic, published by Blackwell Scientific Publications, 2nd Edition, pp. 246-61, 1982 and by William R. Proffit, et al., Contemporary Orthodontics, published by The C. V. Mosby Company, pp. 272-86.

Movement processes related to the configuration of palatal expanders are described by Handelman, *Angle Orthodontic* 67(4): 291-305 and a study by Bishara et al., *Am. J. Orthod. Dentofac, Orthop.*, 91(1): 3-14, 1987. None of these expanders or physiological processes involves the same type of orthopedic movements that we are accomplishing with the retraction devices of this invention. Conventional expansion screws start from a closed position in a side-to-side position in a patient's jaw. Upon adjustment, two or more sections of these screws are spread apart, which in turn widens or spreads apart teeth or jaws. The design of these expansion screws is not to pull teeth, sections of teeth, sections of jaws or jaws together as is required from the retraction devices of our invention.

EXAMPLE 1

Materials and Methods

Animal Study

Forty-eight adult male Sprague-Dawley rats (average body weight of 400 g, 120 days of age) were housed and treated according to a protocol approved by the New York University Institutional Animal Care and Use Committee. Animals were divided into four groups (12 rats per group): control, which received coil spring without activation (C), orthodontic force applied to the spring (O), orthodontic force and soft tissue flap (OF), and orthodontic force, soft tissue flap, and shallow perforations of the buccal cortical plate (OFP). The health status and body weight of the rats were evaluated daily and no significant differences were observed between groups. From each group, 4 animals were used for gene expression studies, 4 for microCT and fluorescent studies and 4 for demineralized histological studies. Procedures were performed on one side of the maxilla, which allowed the contralateral side to be used as an additional control.

Surgical Procedure

On day 0, all groups were anesthetized with intraperitoneal injection of ketamine-xylazine (0.09 mL/100 g) and anesthesia verified by lack of response to toe-pinch. All groups were fitted with 50 cN Sentalloy closing coils (GAC International) tied at both ends to holes drilled in the maxillary incisors and left maxillary first molar with 0.008 in. ligature wire; the coil was activated in groups O, OF, and OFP, but not in C group. In the OF and OFP groups, a soft tissue flap was raised around the left first molar. Flaps were sealed with cyanoacrylate tissue adhesive (Vetbond, 3M). In the OFP group, the animals received three shallow perforations, approximately 0.25 mm in diameter (depth of 0.25 mm), 5 mm mesial to the left first molar using a round bur and hand piece. Animals were checked under general anesthesia twice weekly, and any springs requiring retying (mostly due to continuous eruption of the maxillary incisors) were adjusted. Bone labeling by intraperitoneal injection of calcein (15 mg/kg) was performed on days 0 and 26 and by demeclocycline (25 mg/kg) on day 14. Animals were sacrificed by $CO_2$ narcosis on day 28 and hemimaxillae collected, fixed in formaldehyde for 48 h before storage in 70% ethanol.

Micro-CT Imaging

Hemimaxillae were scanned using a Scanco MicrocCT ($\mu$CT40, Scanco Medical, Basserdorf, Switzerland). Results were analyzed utilizing $\mu$CT V6.0 software on the HP open platform (openVMS Alpha Version 1.3-1 session manager). The area extending from the coronal to the apical root third was analyzed for bony changes. Maxillae were analyzed in fixed coronal and sagittal zones. The ratio of bone volume to total volume (BV/TV) was calculated using a threshold of 275.

Histology and Immunohistochemistry

Hemimaxillae were collected and fixed in 10% phosphate buffer formalin and demineralized in a sodium formate (6.8%) and formic acid (50%) solution for 6-8 weeks. Following demineralization, specimens were dehydrated in alcohol series, embedded in paraffin, and 5-$\mu$m-thick sections cut and stained with hematoxylin and eosin (H&E). Consecutive specimens were immunostained using antibodies for tartarate-resistant acid phosphatase (TRAP; Zymed antibodies, Invitrogen, Carlsbad, Calif.), a marker of osteoclasts, and Vectastain ABC kit (Vector Laboratories, Burlingame, Calif.) according to the manufacturer's instructions. As negative control consecutive sections were exposed to pre-immune serum. Stained sections were scanned on Scan Scope GL series optical microscope (Aperio, Bristol, UK) at 20× magnification. Osteoclasts were defined as TRAP-positive multinuclear cells on the bone surface. The area around the mesiopalatal root of maxillary first molar was divided into mesial and distal halves and osteoclasts in the mesial half were counted. Data were expressed as the number of TRAP positive cells per 1000 $\mu m^2$ in the area of PDL and adjacent alveolar bone, excluding the marrow cavities and blood vessels. For fluorescent microscopy, after formalin fixation specimens were washed overnight in running water, dehydrated in alcohol, cleared in xylene, and embedded in methyl methacrylate according to the method of Erben (Erben, *J Histochem Cytochem* (1997) 45(2):307-13). The samples were sectioned at 5-7 μm thickness on Reichert-Jung Ultracut E microtome and viewed under fluorescent microscopy (Nikon Microscopy, NIS-Elements software).

RT-PCR Analysis

For RNA extraction, 4 animals from each group were sacrificed by $CO_2$ narcosis at 24 hours and the hemimaxillae dissected and frozen in liquid nitrogen. Isolation of total RNA was performed using TRIZOL reagent (Life Technologies, New York, N.Y.), and RNA cleanup was performed using RNeasy Mini Kit (Qiagen Sciences, Valencia, Calif.) as described before (Serafim et al., 2009). All equipment and tools were cleaned with RNaseZap (Sigma, St Louis, Mo.). Ninety-two inflammatory cytokines and cytokine receptor genes were analyzed using primers specific for rat genes (see online appendices for list of genes), using QuantiTect SYBR Green RT-PCR kit (both Qiagen, Valencia, Calif.) on a DNA Engine Optican 2 System (MJ Research, Waltham, Mass.). Each mRNA specimen was tested three times. Relative levels of mRNA were calculated and normalized to the level of GAPDH and acidic ribosomal protein mRNA.

Statistical Analysis

Significant differences between test groups and controls were assessed by analysis of variance (ANOVA). Pairwise multiple comparison analysis was performed using Tukey's post hoc test. Two-tailed p-values were calculated; $p<0.05$ was set as the level of statistical significance.

Results

Osteoperforations Increase the Rate of Tooth Movement

Coil springs were used for mesial movement of the first maxillary molar crown (FIG. 1A). Three shallow perforations were made in the cortical bone, 5 mm mesial to the molar as depicted in FIG. 1B. At 28 days, the average crown movement (measured in 12 rats per group) was 0.29 mm in the O and OF groups (FIG. 1C), significantly different from control ($p<0.05$). The OFP group showed the greatest mean tooth movement, 0.62 mm, which was significantly higher ($p<0.05$) than that of C, O, and OF groups (FIG. 1C).

Osteoperforations Increase Expression of Inflammatory Cytokines

Figure 2B:
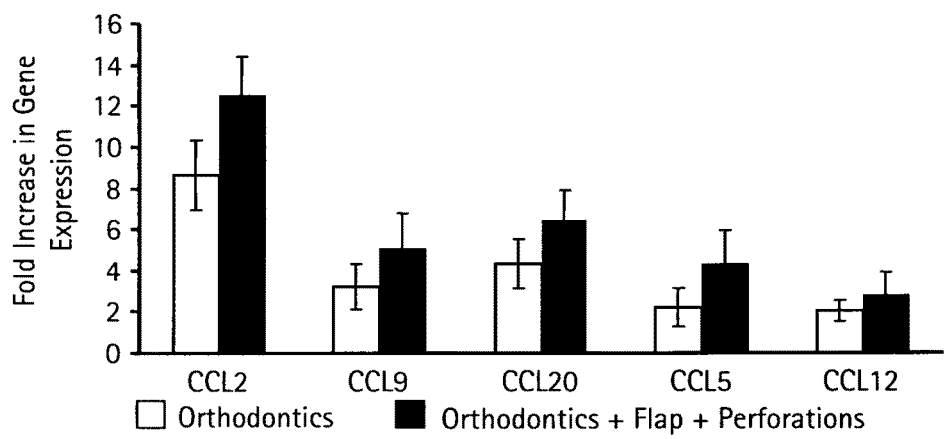
Figure 2C:
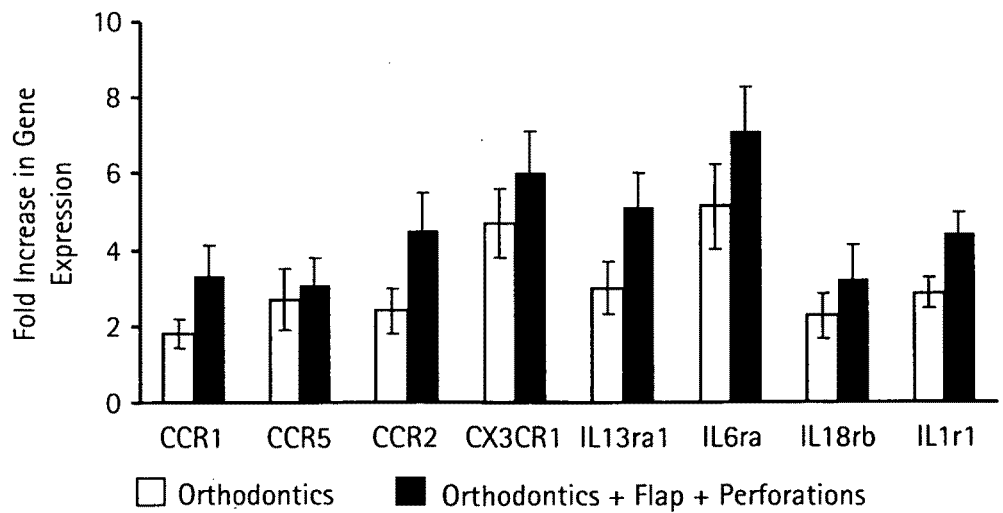

Expression of 92 different cytokines/cytokine receptors was studied by RT-PCR, 24 hours after force application. The expression of 37 cytokines/cytokine receptors increased more than 2-fold in the left maxilla of rats in the O, OF and OFP groups when compared to the C group (data not shown). Differences between O and OF group were not statistically significant. From these 37 cytokines, expression of 21 cytokines/cytokine receptors was statistically higher in the OFP group than in the O or OF groups ($p<0.05$) (FIG. 2), with 8 cytokines showing a 1.6 to 2.7 fold increase (FIG. 2A), 5 chemokines showing a 1.6 to 2.8 fold increase (FIG. 2B), and 8 receptors showing a 1.7 to 2 fold increase in expression (FIG. 2C). All cytokines/cytokine receptors expressed in the OFP group were also expressed in O or OF groups. Expression of cytokines in the contra-lateral side of all groups showed no statistically significant differences from group C (data not shown).

Osteoperforations Increase Osteoclast Activity

Figure 3A:
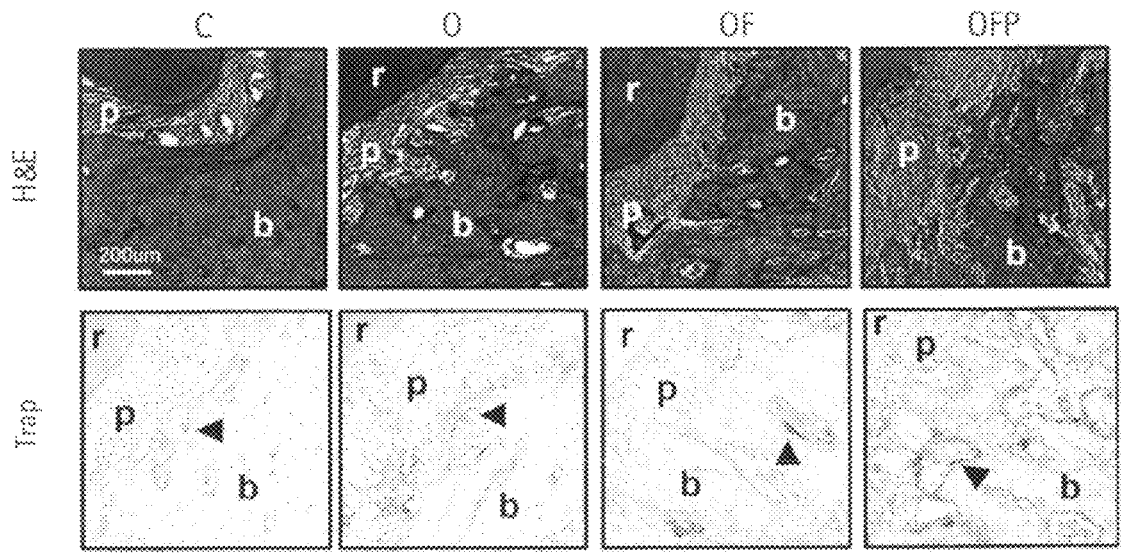
FIG. 3 demonstrates that osteoperforations increase osteoclasts activity (A) Light microphotographs of H&E stained section (Top row) show differences in PDL thickness (p) and alveolar bone resorption (b) in the area of mesio-palatal root of maxillary first molar 28 days post-treatment. TRAP-immunohistochemical staining reveals osteoclasts as brown cells (arrowheads) on the mesial alveolar bone surface in the area of mesio-palatal root of maxillary first molar (Bottom row). (B) High magnification of TRAP positive osteoclast. (C) Changes in number of TRAP-positive cells on the mesial alveolar bone surface of the mesio-palatal root of maxillary first molar. Each value represents the mean±SEM of 4 samples. *Significantly different from C group, **Significantly different from C, O, and OF groups; $p<0.05$.
Figure 3B:
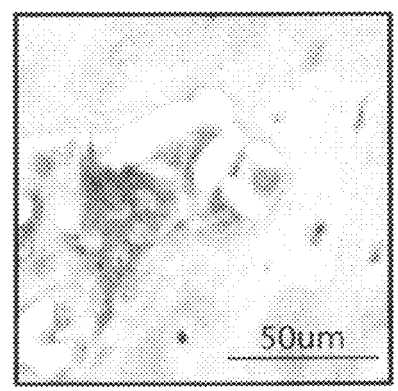
Figure 3C:
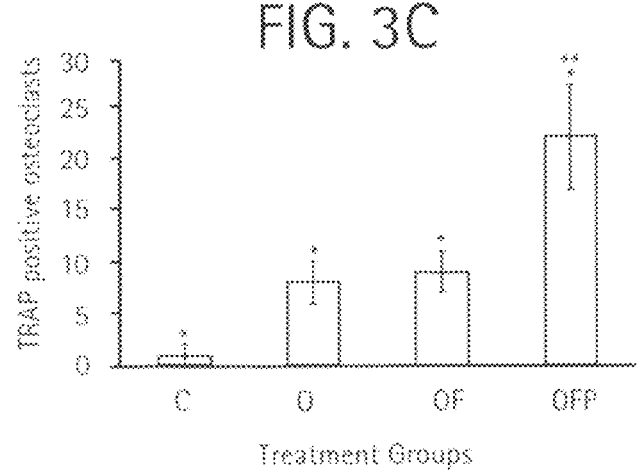

In both O and OF groups, application of the orthodontic force stimulated an increase in alveolar bone resorption in the direction of tooth movement and consequently an increase in PDL thickness (FIG. 3A, top row). The OFP group showed increased alveolar bone resorption in the direction of tooth movement (FIG. 3A, top row). Immunohistochemical staining for TRAP positive osteoclasts (FIG. 3B) revealed an increase in osteoclast number in the OFP group, compared to the OF, and O groups (FIG. 3A, bottom row). Quantitative analysis of osteoclasts in the pressure side (mesial) of alveolar bone adjacent to mesio-palatal root of maxillary first molar demonstrates a 3 fold increase in number of osteoclasts in comparison with O and OF group ($p<0.05$) (FIG. 3C). The difference between number of osteoclasts in O and OF group was not statistically significant.

Figure 4A:
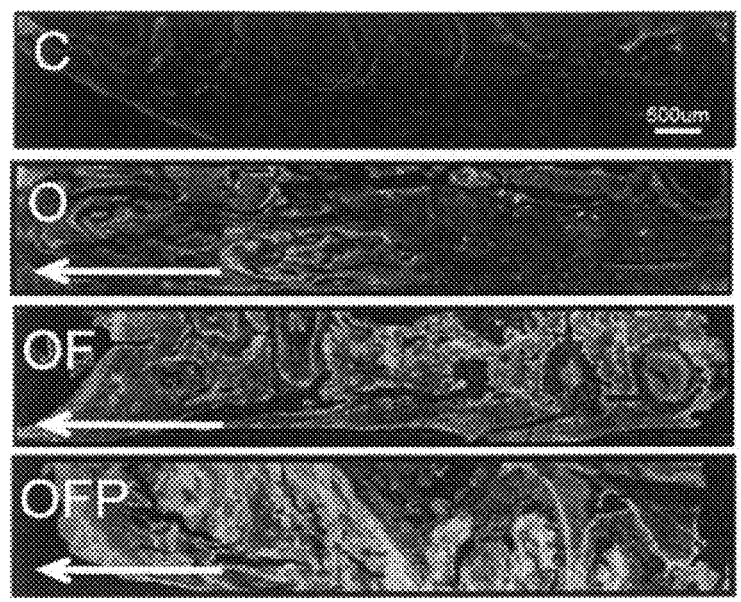
FIG. 4 demonstrates that osteoperforations increase the bone remodeling rate and generalized osteopenia in the entire length of the hemimaxillae. (A) Sagittal sections of maxillae from the four groups viewed under fluorescent microscopy show the rate of bone remodeling in the entire hemimaxilla. The increased intensity of the label in most of the trabecular surface of the OFP group in comparison with other groups indicates that extensive bone remodeling has taken place at 28 days post-treatment. White arrows demonstrate the direction of force application (B) Schematic indicating axial sections (1, 2, 3) and coronal sections (a, b, c) used in the analysis. (C) Representative coronal sections obtained by microCT analysis showing increased trabecular spacing in the OFP group, indicative of bone remodeling activity. White arrows demonstrate the direction of force application. (C=control; O=orthodontic force alone; OF=orthodontic force plus flap; OFP=orthodontic force plus flap plus perforations).
Figure 4B:
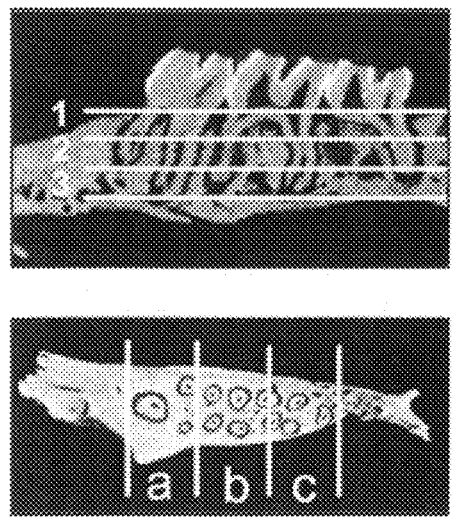
Figure 4C:
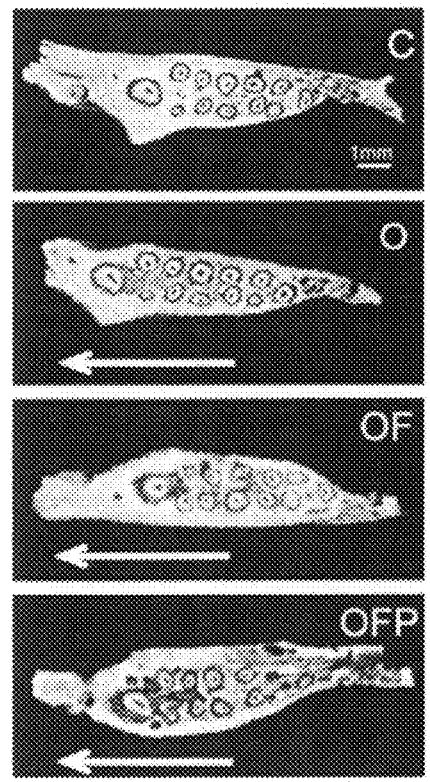
Figure 6:
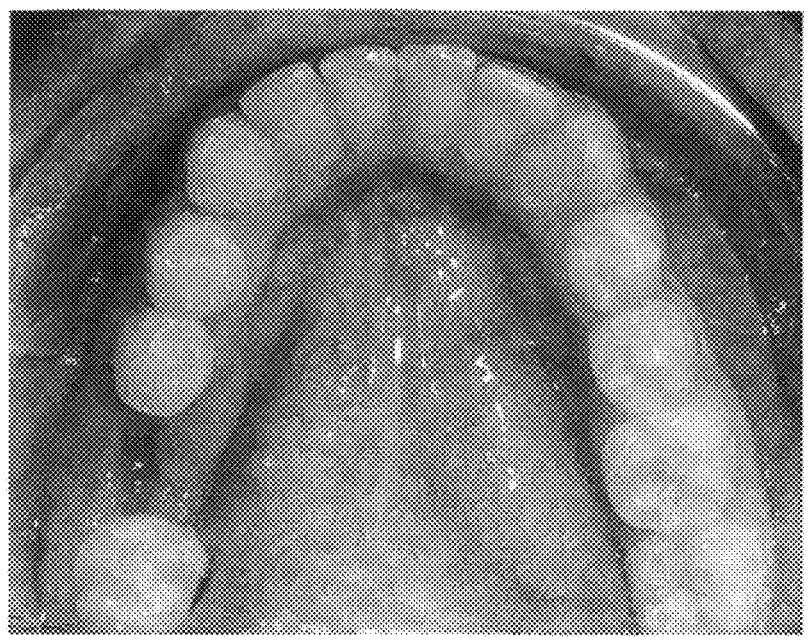
FIG. 6 is a photo of a patient's upper oral cavity showing a space. Historically, to treat a space like this, the orthodontist places a dental implant and crown because protraction of a molar tooth is difficult.
Figure 7:
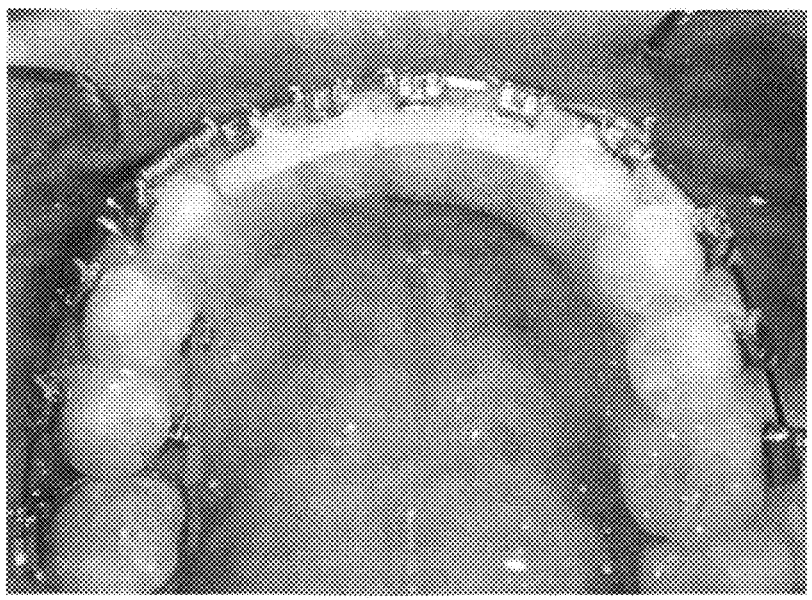
FIG. 7 is a photo of a patient's upper oral cavity showing closure of the space shown in FIG. 6. By applying localized osteoperforations as described in the present invention (2 buccal and 1-2 osteoperforations in the crest of the alveolar bone, the space shown in FIG. 6 was closed with molar protraction in only 8 months.
Figure 8:
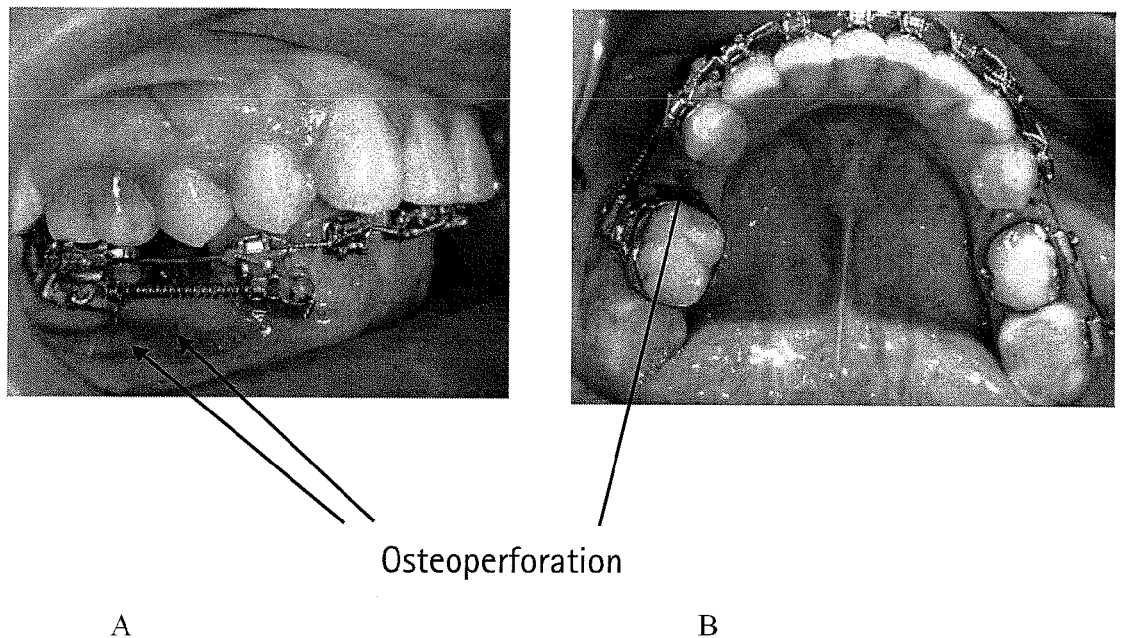
FIG. 8 is a photo depicting that under local anesthetics, small holes (approximately 1.5 mm) may be placed through the attached gingiva, into the bone, without any flap. Minimal bleeding occurs.

Osteoperforations Increase the Rate of Bone Remodeling and Generalized Osteoporosis Sagittal sections of specimens viewed under fluorescent microscopy showed more prominent fluorescence in the OFP group (FIG. 4A), indicative of heightened bone remodeling activity. MicroCT quantification was used to evaluate the effect of osteoperforations on induction of osteoporosity during tooth movement. Comparison of the OFP group with the other groups revealed significant findings on all planes of analysis (FIG. 4B). Bone volume fraction (BV/TV) levels in the OFP group were significantly lower ($p<0.05$, ANOVA) than in the C, O, or OF groups (see online appendices, Table I). BV/TV fraction in control group was on average as high as 82% around first maxillary molar, while in the OFP group these values decrease to 33%. Both O and OF groups also exhibited statistically significant changes in BV/TV levels ($p<0.05$, ANOVA) when compared to the C group. Interestingly, in comparison with other groups, the BV/TV fraction in the OFP group decreased significantly ($p<0.05$) around all left maxillary molars (33% to 35%). This effect was limited to the left hemimaxillae and no change in BV/TV fractions was observed in contra-lateral hemimaxilla ($p>0.05$).

Osteoperforations Induced Generalized Osteopenia

MicroCT quantification was used to evaluate the effect of osteoperforations on induction of osteopenia during tooth movement. Comparison of the OFP group with the other groups displayed significant findings on all planes of analysis (FIG. 5). Bone volume fraction (BV/TV %) levels in the OFP group were significantly lower ($p<0.05$, ANOVA) than that in the C, O, or OF groups, with an extreme of 31.1%. Both O and OF groups also exhibited statistically significant changes in BV/TV % levels ($p<0.05$, ANOVA) when compared to the C group. Interestingly, bone volume fractions in the OFP group were similar in all regions of the rat maxilla, in contrast with the other groups, where a gradient could be observed from the mesial to the distal region. Localized osteoperforations resulted in generalized jaw osteopenia.

CONCLUSIONS

The current results help elucidate the relation between bone injury, inflammation, and tooth movement, and these results demonstrate that the application of minimal injury to the maxilla appears to be sufficient to set in motion an inflammatory cascade that allows accelerated movement of teeth during orthodontic treatment.

EXAMPLE 2

Expected Result of this Study

We expect the flapless shallow perforations that we propose to make to be safe for orthodontic patients. We expect that increasing the local inflammatory response will enhance the rate of tooth movement with no deleterious side effects. We anticipate the elimination of highly invasive surgery as normally required for patients with skeletal moderate class II malocclusion.

Study Design

The subjects will be orthodontic patients with class II division I malocclusion. All subjects will have the upper 1st premolars extracted and placement of TAD mesial to upper 2nd premolar. This is a randomized, single blind, single-center, clinical trial. The randomization process used in this study is stratified randomization. Group A control patients will not receive any osteoperforations and Group B experimental patients will receive right side or left side osteoperforations. The subjects will be assigned in the order they visit the clinic, for example, using ABABAB. Because of inclusion and exclusion criteria, there are no strong confounders.

This will be a single-blind study, only for the investigator(s). Subjects and the resident orthodontist administering the treatment will know the group assignment due to the additional procedure being performed on the experimental group. Orthodontists that are performing the research procedure are investigators in the study. However, casts will be measured to evaluate the rate of tooth movement by investigator who did not treat subjects. Therefore, casts will be measured without the information of subjects' assignment. This approach will minimize investigator bias.

The variables in this study will be levels of inflammatory markers and the rate of tooth movement. At each visit, an impression to evaluate the rate of tooth movement will be taken by measuring casts. Crevicular fluid samples will also be taken from the patients at each visit for evaluation of inflammatory markers using a protein array approach. In addition we will measure probing depth (PD), PI (Plaque Index) and gingival index (GI) to assess periodontal status at each visit. At start of each visit after osteoperforation, patients will be evaluated for level of pain or any discomfort. In this regard, patient will be asked to rate on scale of 1 to 10 the magnitude of pain or other sort of discomfort.

Number of Subjects

A total sample size of 20 patients is being requested for this pilot study with the objective of establishing the safety of the procedure and understanding the levels and variation of inflammatory markers in this patient population. To calculate the sample size a power analysis assuming a type I error frequency of 5% was performed, setting the power of the statistical test at 90% (P=0.9, $\square$=0.1) using results from published data on tooth movement (Verna et al., 1999, Bone: 24, 371) as a guide using the following formula $$N = 2 \cdot (\epsilon/\delta)^2 \cdot (t\alpha, v + t_2(1-p), v)^2$$

Where n=the sample size, e=the population standard deviation, d=the difference that is desired to detect (in this case 50% increase in regular rate of tooth movement ~1.5 mm), α=significance level, v=the degrees of freedom, ta,v=the t value corresponding to α and v, and P=the desired statistical power. Base on this calculation, a sample size of 14 is necessary (7 per group). Considering attrition (for example patients move away, or do not continue treatment), a sample size of 10 per group should be attained.

Age of Subjects

Subjects will be 18-40 years of age. This portion of the population is selected because a large portion of patients undergoing orthodontic treatment are within this age range.

Gender of Subjects

Male patients are included because of the findings in current literature, which suggest that changes in levels of sex hormones can have a significant affect on the rate and range of tooth movement and bone remodeling. (Zittermann, et al., *J Clin Endocrinol Metab* 2000; 85:95-101) Researchers have suggested that orthodontic tooth movement will vary throughout the estrous cycle. (Haruyama, et al., *J Dent Res* 2002; 81:406-410) Males are selected so that confounding variables that are not related to the research question are eliminated.

Racial and Ethnic Distribution

Caucasians will be enrolled in this study. Caucasians that come to the orthodontic clinic are selected to eliminate confounding variables that are not related to the research question. Baseline levels of cytokines in individuals of different races and ethnicities can vary.

Selection Criteria

All subjects will be in good general health, and none will have received periodontal therapy or medication during the past 6 months. Participants will have no history of systemic diseases, periodontal diseases, gingivitis disease or untreated caries. They will not be on any medication that could affect the level of inflammation, such as chronic antibiotics, phenyloin, cyclosporin, anti-inflammatory drugs, systemic corticosteroids, or calcium channel blockers.

Orthodontists will perform a periodontal examination at the beginning of each visit, including probing depth (PD), plaque index (PI) and gingival index (GI) assessment.

To avoid the contamination of crevicular fluid samples with blood, GI and PD will be measured after these collections. All periodontal disease measurements will be performed in four quadrants. PD levels will be measured throughout entire mouth with a periodontal probe calibrated in millimeters each month.

Patient Oral Hygiene Control

If subjects cannot meet inclusion criteria due to poor oral hygiene they will undergo cleaning and oral hygiene education program by hygienist. When oral hygiene improves and they meet all inclusion criteria (PD is <4 mm, GI<1, and PI=1), they can be enrolled into this study. During the study patients will receive oral hygiene instructions and cleanings by hygienist, at each visit.

Inclusion Criteria

1. Caucasian, male subjects ages 18-40 years old who have complete adult dentition, excluding $3^{rd}$ molars, in a skeletal class II division I malocclusion
2. Subjects do not have any systemic diseases
3. PD is <4 mm, GI≤1, and PI≤1
4. If any caries present, patient will be referred to dentist for treatment and maintenance before beginning treatment
5. English speaking Exclusion Criteria 1. Subjects who have taken any antibiotics or periodontal TX in the previous 6 months
2. Subjects who have concomitant medical therapy
3. Subjects with extreme skeletal class II malocclusion: overjet>10 mm, Pg-Nper>18 mm, ANB>7, SN-GoGn>38
4. Female subjects
5. Individuals who are not Caucasian Methods and Procedures This is a randomized, single blind, single-center, clinical trial. The subjects will orthodontic patients with class II division I malocclusion. The subjects will be randomized amongst the two study arms. One treatment arm will receive osteoperforations on the right or left side. The second treatment arm will not receive any osteoperforations. All subjects will have the upper 1st premolar extracted and placement of TAD mesial to upper 2nd premolar. At each visit, we will take an impression to evaluate the rate of tooth movement. We will also collect crevicular fluid samples from the patients at each visit for evaluation of inflammatory markers. The PI, Co-PI, and the student researchers will perform the cytokine analysis. We will also perform an assessment of PD, GI, and PI.

Additional Procedures and Tests that will be performed exclusively for research purposes are:

For the first 6 months Physical data (weight and height), crevicular fluid samples, and assessment of PD, GI, PI will be collected.

6 months after extraction we will initiate treatment of topical anesthesia and placement of 3 tiny holes in the bone that surrounds upper canine (right or left). The following 6 months, at every visit physical data (weight and height), crevicular fluid samples, impressions, and assessment of PD, GI, PI will be collected.

Time for Recruitment

A total sample size of 20 subjects is being requested for this pilot study. A chart review was conducted at the New York University College of Dentistry Department of Orthodontics. 4 patients every week that are seen in the Department of Orthodontics will meet the selection criteria for the study. It is estimated that 20% of the patients (32 patient) will be willing to participate in the study, therefore we expect it will take up to 1 year to recruit 20 patients.

Evaluation for Recruitment

Periodontal evaluation of prospective subjects (Class II, Division 1 patients free of systemic disease) will be performed by orthodontists in the Clinic of the Department of Orthodontics and include (based on American Association of Peridontists' guidelines) including a full mouth series, and a full mouth probing depth (PD), plaque index (PI) and gingival index (GI) assessment.

Detailed Technical Plan

Phase 1:

Physical Data

Every month, the weight and height of the subject will be measured and recorded. The purpose of recording these measurements is to reduce confounders.

Sampling Gingival Crevicular Fluid (GCF)

GCF samples will be collected from each patient at each visit to evaluate inflammation levels. GCF samples in both the experimental and control groups will be collected between 10:00 am and 12:00 μm. Before any treatment begins, sample of crevicular fluid will be taken from maxillary mesial and distal upper canines that are affected by the retraction. Samples will be taken bilateral mesial and distal to upper canine. Prior to sampling, we will remove supragingival plaque. Cotton rolls will isolate the regions where GCF samples will be taken. The teeth and marginal gingiva will be dried with air before sampling. Filter paper strips will be inserted 1 mm below the gingival margin into the mesio labial and mesio labial crevices surrounding each tooth for 30 seconds. About 1.2 μL to 3 μL of GCF will be collected from each side of the tooth on the paper strip. This will provide about 1,200,000 pg to 3,000,000 pg of GCF that will be diluted to obtain the 50 to 100 μL of sample required for analysis using glass slide-based arrays. GCF samples will be stored in −70° C. refrigerator in a laboratory on $10^{th}$ floor, room #1038 NYU College of Dentistry that will be locked.

Taking Impression

Impression will be taken with Alginate. The procedure of taking impression will be done before wire placement. After taking impression, immediately Anhydrite ($CaSO_4$) will be poured over the impression. The casts will be labeled (patient number and date) and stored and locked in a laboratory.

X-Ray

Peri-apical x-ray will be taken at enrollment, the day of the TAD placement and perforation, 3 and 6 months later evaluate the bone situation, estimate the placement of TADs and perforation, and evaluate bone after tiny perforations and tooth movement.

The subjects' x-ray exposure will be carefully monitored and maintained at safe levels. This study will require no additional x-ray exposure than what would be required with traditional orthodontics treatment. The effective doses that subjects will be exposed will be well within the annual effective dose limit of 1 mSv. The effective dose for a lateral cephalometric x-ray is 0.002-0.003 mSv. The effective dose for a periapical x-ray is 0.001-0.008 mSv. The effective dose for a panoramic x-ray ranges from 0.002-0.03 mSv. (Whaites, *Dental Radiography and Radiology*, London: Churchill Livingstone Elsevier, 2007; Association AD. *Oral Health Topics A to Z;* 2009) The estimated effective dose for a bitewing dental radiograph is 0.038. Throughout the study the patient will have a panoramic x-ray (0.03 mSv) at the beginning of treatment. In addition the subject will have bitewing dental radiographs (0.038 mSv) taken every 3 months. The total effective dose exposure will be much less than the recommended effective dose limit of 1 mSv.

Initial Treatment

Orthodontic treatment will begin with alignment of teeth into proper position with subsequent distal translational movements until proper positioning of teeth has been achieved. Orthodontic appliances consisting of Innovation brackets (GAC International) will be bonded on upper incisors, lateral incisors, 2nd premolars, $1^{st}$ molars and $2^{nd}$ molars. Due to their occlusion (Class II Division I) we will treat upper arch first. Occasionally bands will be cemented on maxillary first molars. The ordinal wire sequence will consist of first using 0.016NiTi, then 0.016×0.022NiTi archiwires, for initial brackets leveling. And after that, 0.016×0.022 stainless steel will be used for canine retraction.

Each wire will be used for 2 months.

Phase 2

The PI, Co-PI, or the residents assigned to the study will evaluate these conditions of subject's occlusion before initiating phase 2. The wire must be, 0.016×0.022 stainless steel and no tooth rotations may be present.

Anesthesia

Before tiny perforations procedure, orthodontists will deliver the local anesthetic. The local anesthetic that will be used is lidocaine with 1:100,000 epinephrine. The dentist will administer an inferior alveolar nerve block (IANB) and a buccal nerve block to anesthetize the tooth to be treated. A 27-gauge, long needle will be used and after multiple negative aspirations, 1.5 ml of anesthetic will be deposited. More anesthetic will be delivered and documented as needed. Patient will be given a complete cleaning at every visit after all measurements.

TADs Procedure

The mini screw implants (TADs) (GAC International) will be prepared (see appendix). The entire procedure will be carried out under profuse saline irrigation at room-temperature. After procedure of anesthesia, we will insert implants between upper buccal $1^{st}$ and $2^{nd}$ premolar areas.

Perforation

Surgical perforation procedure will be performed following TADs placement. In the alveolar bone, three small holes will be made mesial to $2^{nd}$ premolar, perpendicular to the tooth. These 3 tiny holes will form a line (facial to palatal) along the bone.

Appliance

The coil (GAC International) will be connected to an attachment on canine bracket to the TAD. The force will be adjusted to 100 g at all visits.

Orthodontic Treatment

Before the engagement of appliance, 0.016×0.022 ss wire will be in place for two months. This wire will be the base wire for the retraction of canine. This arch wire is of reasonable for strength.

Lab Procedure

Measurement of Casts

Measurements will be taken from the most convex point of canine to the same point of $1^{st}$ premolar, in mm. This will be done by investigator/s who did not treat patients directly, in order to maintain a single blind study.

Determine Volume of GCF Sample:

An electronic gingival fluid-measuring device, the Periotron 8000, will be used to measure the volume of the GCF samples collected from each patient at every visit. We will calibrate the Periotron 8000 with standard volumes of human serum. The Periotron 8000 will be calibrated according to the manufacturer's instructions.[8] The minimum concentration of for each cytokine must be between 5 pg/mL and 45 pg/mL in each sample for detection using Glass-slide based array method.

The GCF samples will be placed into microcentrifuge tubes and diluted to 0.1 ml with buffer solution provided in the RayBio® Human Cytokine Antibody Array kit. The paper strips must be incubated for 1 hour in the buffer solution at 4° C. Then, we will use centrifugation (14,000×g for 5 minutes) to collect the fluid from the paper strip. Paper strips in sealed microcentrifuge tubes will be labeled and stored at −20° C. until analysis. The microcentrifuge tubes will be labeled with the date, patient's number, the tooth number from which the sample was collected. Prior to analysis GCF samples, will be thawed and recentrifuged. GCF samples will then be analyzed according to the RayBio® Human Cytokine Antibody Array kit (see appendix II).

Data Analysis and Monitoring

The specific aim is to determine the effect of administering shallow perforations. The dependent variables, levels of inflammatory markers will be measured using a Human Cytokine Antibody Array kit, and tooth movement; will be measured using in the casts and analyzed using the t-test. Measurements of casts and Cytokine Antibody Array will be performed by investigators blinded to the group assignment of each patient. Data will be plotted using Excel spreadsheet before statistical analysis.

Results

The results will demonstrate the role of shallow, small perforations in the levels of inflammatory markers and the rate of tooth movement. The patients that receive osteoperforation, in addition to orthodontics treatment, will finish their treatment in significantly shorter period of time. This will decrease the potential side effects associated with any lengthy orthodontics treatment such as root resorption, loss of alveolar bone, white spots on enamel due to demineralization around brackets and gingivitis.

EXAMPLE 3

A 12 year old Caucasian male was referred for treatment of moderate upper and lower crowding and excessive overjet and overbite. He was near the finishing stage of his orthodontic treatment at the age of 14. His Pedodontist recommended extraction of the lower right first molar due to severe caries. The extraction of the lower right first molar produced a 12 mm excessive space between the lower right second premolar and the lower right second molar. Therefore, either preserving the space of the lower first molar for a future implant or protracting the lower second molar was required. There was a space of almost 12 mm to replace the lower first molar. Since the patient was near to finishing orthodontic treatment, protracting the lower second molar with traditional orthodontic treatment would lengthen the treatment for at least 12-16 months. On the other hand, preserving the space for future implant replacement required the patient to wear retainers for an additional 4 to 5 years until growth and development completely stopped around the age of 18-20.

Therefore after consultation, we decided to protract the lower second molar and to shorten the time of treatment by osteoperforation. Three osteoperforations having a depth of 4-6 mm and a width of 1.5 mm were performed between the lower right second molar and the lower right second premolar, using a hand-held device. Then, the orthodontic force was applied for protraction of the lower second molar. The total procedure took less than 5 minutes without any flap or excessive bleeding. No analgesic or extra care other than mouth wash was prescribed and a close follow up of the patient during the next few months did not reveal any discomfort or side effects. This osteoperforation was repeated after two months. After 5 months from the first osteoperforation, the space between the lower right second molar and the lower right second premolar was completely closed. This perforation procedure decreases the length of treatment from about 12 months to about 5 months.

EXAMPLE 4

A 24 year old Caucasian male with severe shift of the upper anterior teeth to the right (5-6 mm) was referred. The lower arch needed minimum orthodontics treatment for correction of moderate crowding. Correction of the upper midline discrepancy with such a degree of severity requires extraction of the upper left first premolar followed by retraction of the canine which thereby provides enough space for correction of the midline. The treatment time for such a procedure was estimated at about 2 years. We suggested accelerating the rate of tooth movement with osteoperforation. Orthodontics treatment was begun, and the patient was referred for extraction of the upper left first premolar. After initial leveling and aligning, three osteoperforations having a depth of 4-6 mm and a width of 1.5 mm were performed between the upper left canine and the upper left second premolar. The total procedure took less than 5 minutes without any flap or excessive bleeding. No analgesic or extra care other than mouth wash was prescribed, and close follow up of the patient during the next few months did not reveal any discomfort or side effects. This procedure was repeated after 2 months. The canine tooth was retracted with conventional methods. Complete Canine retraction was accomplished in 3 months. Another osteoperforation between the upper left canine and the upper left lateral was performed for retraction of the other anterior teeth accomplished in another 3 months. Finishing and detailing required an additional 3 months. The patient's complete treatment required less than one year (11 months). This osteoperforation treatment reduced the patient's length of treatment from about 24 months to 11 months.

EXAMPLE 5

A 38 year old African American female patient was referred due to congenital missing of the upper laterals and excessive spacing in the upper and lower. While the patient had moderate orthodontic problems in both the upper and lower arches, her main concern was the missing upper lateral teeth. For a long time she had been replacing these teeth with an upper partial denture. Two options were to either replace the upper laterals with an implant after making space for the upper laterals during orthodontics treatment or protracting the posterior teeth forward and replacing the upper laterals with natural teeth. The patient preferred the second option. The length of treatment for this procedure was estimated at around two years. We decided to shorten the treatment time using osteoperforation. After placement of fixed appliance (braces) and initial leveling and aligning, osteoperforation was performed in the area of the missing laterals by four perforations in each side having 4-6 mm depth and 1.5 width using a hand instrument. The total procedure took less than 5 minutes without any flap or excessive bleeding. No analgesic or extra care other than mouth wash was prescribed, and close follow up of patient during the next few months did not reveal any discomfort or side effects. Protraction of the posterior teeth was accomplished using conventional mechanics. The treatment was accomplished in 13 months. This osteoperforation procedure reduced the patient treatment time from about 24 months to 13 months.

EXAMPLE 6

A 45 year old Hispanic female was referred by another orthodontist due to the severity of the case and failure of previous orthodontic treatment. The patient had a very severe deep bite that was impinging on the lower gingiva, very dense bone around the upper anterior teeth and retroclined upper teeth. The previous orthodontist tried to correct the deep bite for 3 years with no success. After evaluation of bone density around the upper anterior teeth, we decided to induce temporary osteopenia by osteoperforation and combine that with intrusion and retraction forces on the upper anterior teeth. The patient received osteoperforation between the upper anterior teeth, 3 in each space between the anterior teeth, and each being 4-6 mm deep and 1.4 mm wide. The total procedure took less than 5 minutes without any flap or excessive bleeding. No analgesic or extra care other than mouth wash was prescribed, and close follow up of the patient during the next few months did not reveal any discomfort or side effects. This procedure was combined with conventional orthodontics to intrude and retract the anterior teeth. The overbite was corrected after 4 months, and the remaining orthodontic treatment was accomplished in 7 months. Therefore, the total treatment lasted for 11 months. While conventional therapy without osteoperforation after 3 years failed, osteoperforation in combination with orthodontic treatment corrected the patient's malocclusion in 11 months.

We claim:

1. A method of moving a tooth to a desired position within a patient's mouth comprising:
   a) perforating or pricking tissue in the oral cavity adjacent the tooth to be moved sufficient to induce an inflammatory response in the tissue wherein the perforating or pricking is performed 1 to 5 mm from the alveolar crest to produce perforations, wherein none of the perforations penetrate medullary bone, wherein all of the perforations extend through gingival tissue into cortical bone, and wherein expression of one or more inflammatory markers is increased in the tissue by at least 50% as compared to the expression of the one or more inflammatory markers prior to any perforations; and
   b) installing an orthodontic appliance in the patient's mouth to exert force on the tooth in the direction of the desired position.

2. The method of claim 1 further comprising providing an orthodontic appliance on or near the tooth to be moved.

3. The method of claim 2 wherein the orthodontic appliance is installed on the tooth within about one day of perforating.

4. The method of claim 1 wherein 1 to 15 perforations are made in the tissue of the oral cavity.

5. The method of claim 1 wherein the perforations are 0.5 to 1.5 mm in diameter.

6. The method of claim 1 wherein the perforations are 1 to 6 mm deep.

7. The method of claim 1 wherein the perforations are placed 0.1 to 10 mm distance from each other.

8. The method of claim 1 wherein the one or more inflammatory marker is one or more cytokine, one or more chemokine, or one or more inflammatory receptor selected from the group consisting of CCL20, CCR1, ILTa, IL-3, CCL5, CCR5, CX3CR1, IL-18rb, IL-1r1, IL-1, IL-6, IL-18, IL-6ra, TNF, IL-11, IL13ra1, CCL2, CCL9, and CCL12.

9. The method of claim 1 wherein TRAP-positive osteoclasts are increased by at least 50% in number in tissue proximate the perforations as compared to the number of TRAP-positive osteoclasts prior to any perforations.

10. A method of moving a tooth to a desired position within a patient's mouth according to claim 1 wherein the patient experiences minimal or no bleeding.

11. A method of moving a tooth to a desired position within a patient's mouth comprising:
    a) performing osteoperforations by rinsing the oral cavity with a chemical antiseptic, applying a local anesthetic, and making small perforations adjacent the tooth to be moved having a depth of 0.5 to 3 mm in tissue in the patient's mouth wherein the perforations are placed 1 to 5 mm from the alveolar crest wherein none of the perforations penetrate medullary bone, wherein all of the perforations extend through gingival tissue into cortical bone, and wherein expression of one or more inflammatory markers in the tissue is increased by at least 50% as compared to the expression of the one or more inflammatory markers prior to any perforations; and
    b) installing an orthodontic appliance in the patient's mouth to exert force on the tooth in the direction of the desired position.

12. The method of claim 11 wherein 1 to 15 perforations are made in the tissue of the oral cavity.

13. The method of claim 11 wherein the perforations are 0.5 to 1.5 mm in diameter.

14. The method of claim 11 wherein the perforations are 1 to 6 mm deep.

15. The method of claim 11 wherein the perforations are placed 0.1 to 10 mm distance from each other.

16. The method of claim 11 wherein the one or more inflammatory marker is one or more cytokine, one or more chemokine, or one or more inflammatory receptor selected from the group consisting of CCL20, CCR1, ILTa, IL-3, CCL5, CCR5, CX3CR1, IL-18rb, IL-1r1, IL-1, IL-6, IL-18, IL-6ra, TNF, IL-11, IL13ra1, CCL2, CCL9, and CCL12.

17. The method of claim 11 wherein TRAP-positive osteoclasts are increased in number by at least 50% in tissue proximate the perforations as compared to the number of TRAP-positive osteoclasts prior to any perforations.

18. A method of moving a tooth to a desired position within a patient's mouth according to claim 11 wherein the patient experiences minimal or no bleeding.

19. A method of moving a tooth to a desired position within a patient's mouth comprising:
    a) perforating or pricking tissue in the oral cavity sufficient to induce an inflammatory response in the tissue wherein the perforating or pricking is performed 1 to 5 mm from the alveolar crest adjacent the tooth to be moved to produce perforations, wherein none of the perforations penetrate medullary bone, wherein all of the perforations extend through gingival tissue into cortical bone, and wherein TRAP-positive osteoclasts are increased in number by at least 50% in tissue proximate the perforations as compared to the number of TRAP-positive osteoclasts prior to any perforations; and b) installing an orthodontic appliance in the patient's mouth to exert force on the tooth in the direction of the desired position.

20. A method of moving a tooth to a desired position within a patient's mouth according to claim 19 wherein the patient experiences minimal or no bleeding.

21. A method of moving a tooth to a desired position within a patient's mouth comprising:

a) performing osteoperforations by rinsing the oral cavity with a chemical antiseptic, applying a local anesthetic, and making small perforations having a depth of 0.5 to 3 mm in tissue in the patient's mouth wherein the perforations are placed 1 to 5 mm from the alveolar crest adjacent the tooth to be moved, wherein none of the perforations penetrate medullary bone, wherein all of the perforations extend through gingival tissue into cortical bone, and wherein TRAP-positive osteoclasts are increased in number by at least 50% in tissue proximate the perforations as compared to the number of TRAP-positive osteoclasts prior to any perforations; and b) installing an orthodontic appliance in the patient's mouth to exert force on the tooth in the direction of the desired position.

22. A method of moving a tooth to a desired position within a patient's mouth according to claim 21 wherein the patient experiences minimal or no bleeding.

\* \* \* \* \*